United States Patent [19]
Zhang et al.

[11] Patent Number: 5,670,483
[45] Date of Patent: Sep. 23, 1997

[54] STABLE MACROSCOPIC MEMBRANES FORMED BY SELF-ASSEMBLY OF AMPHIPHILIC PEPTIDES AND USES THEREFOR

[75] Inventors: Shuguang Zhang, Cambridge; Curtis Lockshin, Lexington; Alexander Rich; Todd Holmes, both of Cambridge, all of Mass.

[73] Assignee: Massachusetts Insititute of Technology, Cambridge, Mass.

[21] Appl. No.: 346,849

[22] Filed: Nov. 30, 1994

Related U.S. Application Data

[63] Continuation of Ser. No. 973,326, Dec. 28, 1992, abandoned.

[51] Int. Cl.$^6$ .............. A61K 7/08; A61K 14/00; C07K 38/10; C07K 38/16
[52] U.S. Cl. .............. 514/14; 514/12; 514/13; 530/300; 530/324; 530/325; 530/326; 530/327; 530/350
[58] Field of Search .............. 530/300, 350; 514/12, 13, 14

[56] References Cited

U.S. PATENT DOCUMENTS 5,080,936  1/1992  Cerwen ............... 427/322

FOREIGN PATENT DOCUMENTS 4221394  8/1992  Japan.
4221395  8/1992  Japan.

OTHER PUBLICATIONS

Smith, G.G. et al.; J. Pharm. Sci. 65:727–732 (1976).
Physician's Desk Reference 47th Edition, Medical Economics Data, Montvale, NJ., 1993, p. 2598.
WPI Accession No. 92–313678/38 (abstract of JP 4–221394).
WPI Accession No. 92–313679/38 (abstract of JP 4–221395).
Zhang et al., "Zuotin, a putative Z–DNA binding protein in *Saccharomyces cerevisiae*", *The EMBO J.* 11(10):3787–3796 (1992).
Osterman, D.G. and Kaiser, E.T., "Design and Characterization of Peptides with Amphiphilic β–Strand Structures", *J. Cell. Biochem.* 29:57–72 (1985).
Brack, A. and Orgel, L.E., "βstructures of alternating polypeptides and their possible prebiotic significance", *Nature* 256:383–387 (1975).

(List continued on next page.)

*Primary Examiner*—Eric Grimes
*Attorney, Agent, or Firm*—Hamilton, Brook, Smith & Reynolds, P.C.

[57] ABSTRACT

Described herein is the self-assembly of amphiphilic peptides, i.e., peptides with alternating hydrophobic and hydrophilic residues, into macroscopic membranes. The membrane-forming peptides are greater than 12 amino acids in length, and preferably at least 16 amino acids, are complementary and are structurally compatible. Specifically, two peptides, $(AEAEAKAK)_2$ $(ARARADAD)_2$, were shown to self-assemble into macroscopic membranes. Conditions under which the peptides self-assemble into macroscopic membranes and methods for producing the membranes are also described. The macroscopic membranes have several interesting properties: they are stable in aqueous solution, serum, and ethanol, are highly resistant to heat, alkaline and acidic pH, chemical denaturants, and proteolytic digestion, and are non-cytotoxic. The membranes are potentially useful in biomaterial applications such as slow-diffusion drug delivery systems, artificial skin, and separation matrices, and as experimental models for Alzheimer's disease and scrapie infection. The sequence of the peptide, EAK16, was derived from a putative Z-DNA binding protein from yeast, called zuotin. The cloning and characterization of the ZUO1 gene are also described.

48 Claims, 14 Drawing Sheets

OTHER PUBLICATIONS

Brack, A. and Caille, A., "Synthesis and β–Conformation of Copolypeptides with Alternating Hydrophilic and Hydrophobic Residues":, *Int. J. Peptide Protein Res.* 11:128–139 (1978).

Brack, A. and Barbier, B., "Early Peptidic Enzymes", *Adv. Spac. Res.* 9(6): (6)83–(6)87 (1989).

Marqusee S. and Baldwin, R.L., "Helix stabilization by Glu$^-$... Lys$^+$ salt bridges in short peptides of *de novo* design", *Proc. Natl. Acad. Sci. USA* 84:8898–8902 (1987).

Marqusee, S., et al., "Unusually stable helix formation in short alanine–based peptides", *Proc. Natl. Acad. Sci. USA* 86:5286–5290 (1989).

Padmanabhan, S., et al., "Relative helix–forming tendencies of nonpolar amino acids", *Nature* 344:268–270 (1991).

Seipke, G., et al., "Synthesis and Properties of Alternating Poly(Lys–Phe) and Comparison with the Random Copolymer Poly(Lys$^{51}$, Phe$^{49}$)", *Biopolymers* 13:1621–1633 (1974).

St. Pierre, S., et al., "Conformational Studies of Sequential Polypeptides Containing Lysine and Tyrosine", *Biopolymers* 17:1837–1848 (1978).

Peggion, E., et al., "Conformational Studies on Polypeptides. The Effect of Sodium Perchlorate on the Conformation of Poly–L–lysine and of Random Copolymers of L–Lysine and L–Phenylalanine in Aqueous Solution",*Biopolymers* 11:633–643 (1972).

Trudelle, Y., "Conformational study of the sequential (Tyr–Glu)$_n$ copolymer in aqueous solution", *Polymer* 16:9–15 (1975).

Rippon, W.B., et al., "Spectroscopic Characterization of Poly(Glu–Ala)", *J. Mol. Biol.* 75:369–375 (1973).

Gay, N.J., et al., "A leucine–rich repeat peptide derived from the *Drosophila* Toll receptor forms extended filaments with a β–sheet structure", *FEBS* 291(1):87–91 (1991).

Hilbich, C., et al., "Aggregation and Secondary Structure of Synthetic Amyloid βA4 Peptides of Alzheimer's Disease", *J. Mol. Biol.* 218:149–163 (1991).

Halverson, K., "Molecular Determinants of Amyloid Deposition in Alzheimer's Disease: Conformational Studies of Synthetic β–Protein Fragments", *Biochemistry* 29:2639–2644 (1990).

Gasset, M., et al., "Pertubation of the secondary structure of the scrapie prion protein under conditions that alter infectivity", *Proc. Natl. Acad. Sci. USA* 90:1–5 (1993).

Lizardi, P.M., "Genetic Polymorphism of Silk Fibroin Studied by Two–Dimensional Translation Pause Fingerprints", *Cell* 18:581–589 (1979).

Thomas, E.L., "Gigamolecules in Flatland", *Science* 259:43–45 (1993).

Stupp, S.I., "Synthesis of Two–Dimensional Polymers", *Science* 259:59–63 (1993).

Gulik–Krzywicki, T., et al., "Electron microscopic study of supramolecular liquid crystalline polymers formed by molecular recognition–directed self–assembly from complementary chiral components", *Proc. Natl. Acad. Sci. USA* 90:163–167 (1993).

```
MFSLPTLTSD ITVEVNSSAT KTPFVRRPVE PVGKFFLQHA QRTLRNHTWS EFERIEAEKN   60
VKTVDESNVD PDELLFDTEL ADEDLLTHDA RDWKTADLYA AMGLSKLRFR ATESQIIKAH  120
RKQVVKYHPD KQSAAGGSLD QDGFFKIIQK AFETLTDSNK RAQYDSCDFV ADVPPKKGT   180
DYDFYEAWGP VFEAEARFSK KTPIPSLGNK DSSKKEVEQF YAFWHRFDSW RTFEFLDEDV  240
PDDSNRDHK RYIERKNKAA RDKKKTADNA RLVKLVERAV SEDPRIKMFK EEEKKEKERR   300
KWEREAGARA EAEAKAKAEA EAKAKAESEA KANASAKADK KKAKEAAKAA KKKNKRAIRN  360
SAKEADYFGD ADKATTIDEQ VGLIVDSLND EELVSTADKI KANAAGAKEV LKESAKTIVD  420
SGKLPSSLLS YFV
```

K-D: ionized pair interaction
    distance = 5 + 3 = 8

Q-Q: hydrogen bonding
    distance = 4 + 4 = 8

Peptide A   N-VRVRVDVDVRVRVDVD-c
Peptide B             c-KAKADADAKAKADADA-n

R (6) + D (3) = 9
D (3) + K (5) = 8

Peptide A   N-VRVRVDVDVRVRVDVD-c
Peptide A             c-DVDVRVRVDVDVRVRV-n

Peptide B   N-ADADAKAKADADAKAK-c
Peptide B             c-KAKADADAKAKADADA-n

FIG.7C

STABLE MACROSCOPIC MEMBRANES FORMED BY SELF-ASSEMBLY OF AMPHIPHILIC PEPTIDES AND USES THEREFOR

RELATED APPLICATION

This application is a continuation of application Ser. No. 07/973,326 filed on Dec. 28, 1992, now abandoned, which is incorporated herein by reference in its entirety.

GOVERNMENT FUNDING

This work was supported by Grant No. NIH-5R37-CA04186 from the National Institutes of Health, and by Grant No. N00014-90-3-9075 from the office of Naval Research. The U.S. Government has certain rights in this invention.

BACKGROUND

Macroscopic membranes play an important role in many biological processes at both the cellular and organismic level. In addition, membranes are used in a number of medical, research, and industrial applications. Physiologically compatible membranes would be especially valuable for biomedical products. At present, the self-assembly of peptides into macroscopic membranes has not been reported.

SUMMARY OF THE INVENTION

A small peptide termed EAK16 (AEAEAKAKAEAEAKAK310-325of SEQ ID NO:2) was discovered serendipitously to self-assemble into stable macroscopic membranes in the presence of millimolar concentrations of salt. This invention relates to the self-assembly of peptides into stable macroscopic membranes. Peptides which form membranes are characterized as being amphiphilic, i.e., having alternating hydrophobic and hydrophilic amino acid residues; greater than 12 amino acids, and preferably at least 16 amino acids; complementary and structurally compatible. Complementary refers to the ability of the peptides to interact through ionized pairs and/or hydrogen bonds which form between their hydrophilic sidechains, and structurally compatible refers to the ability of complementary peptides to maintain a constant distance between their peptide backbones. Peptides having these properties participate in intermolecular interactions which result in the formation and stabilization of β-sheets at the secondary structure level and interwoven filaments at the tertiary structure level.

Both homogeneous and heterogeneous mixtures of peptides characterized by the above-mentioned properties can form stable macroscopic membranes. Peptides which are self-complementary and self-compatible can form membranes in a homogeneous mixture. Heterogeneous peptides, including those which cannot form membranes in homogeneous solutions, which are complementary and/or structurally compatible with each other can also self-assemble into macroscopic membranes.

Peptides which can self-assemble into macroscopic membranes, the conditions under which membrane formation occurs, and methods for producing the membranes are described and included in this invention.

Macroscopic membranes formed of the peptide EAK16 have been found to be stable in aqueous solution, in serum, and in ethanol and are highly resistant to degradation by heat, alkaline and acidic pH (i.e., stable at pH 1.5–11), chemical denaturants (e.g., guanidine-HCl, urea and sodium dodecyl sulfate), and proteases (e.g., trypsin, α-chymotrypsin, papain, protease K, and pronase). The membranes have also been found to be non-cytotoxic. The membranes are thin, transparent and resemble high density felt under high magnification. Being composed primarily of protein, the membranes can be digested and metabolized in animals and people. They have a simple composition, are permeable, and are easy and relatively inexpensive to produce in large quantities. The membranes can also be produced and stored in a sterile condition. Thus, the macroscopic membranes provided by this invention are potentially useful as biomaterial for medical products, as vehicles for slow-diffusion drug delivery, as separation matrices, and for other uses requiring permeable and water-insoluble material.

Furthermore, the salt-induced assembly of the peptides into insoluble and protease-resistant protein filaments with a β-sheet secondary structure is similar in some respects to the formation of the neurofibrillary filaments and amyloid plaques associated with Alzheimer's disease and the formation of scrapie prion protein filaments. The formation of the macroscopic membranes can therefore be useful as a model system to study these pathological processes. For example, such a model system can be used to identify drugs which inhibit filament formation and are thus potentially useful for treating Alzheimer's disease and scrapie infection.

Peptide EAK16 was derived from a region of a yeast protein, zuotin, which exhibits a high affinity for DNA in the left-handed Z conformation. Zuotin was identified by a gel shift assay for Z-DNA binding proteins developed by the Applicants. Applicants further cloned and sequenced the gene encoding zuotin. Characterization of zuotin revealed that the protein is a potential substrate for several protein kinases and identified a putative DNA-binding domain. This invention also includes all or biologically active portions of the zuotin protein and DNA encoding zuotin.

BRIEF DESCRIPTION OF THE DRAWINGS

FIG. 1 shows the amino acid sequence of zuotin (SEQ. ID NO:2) and a number of features of this protein.

FIG. 7A illustrates the self-complementarity and self-compatibility of a peptide (SEQ ID NO:19).

FIG. 7B illustrates staggering of interacting peptides.

FIG. 7C illustrates peptide interactions in a heterogeneous mixture (SEQ ID NO:20 and 21).

DETAILED DESCRIPTION OF THE INVENTION

This invention is based on the serendipitous discovery that a small synthetic peptide, EAK16 (AEAEAKAKAEAEAKAK; 310-325of SEQ ID NO:2), self-assembles into macroscopic membranes in an aqueous solution containing a small amount of salt. The sequence of EAK16 was originally found in a region of alternating hydrophobic and hydrophilic residues in a yeast protein called zuotin (heavily underlined in FIG. 1). When EAK16 was added to the medium of cultured nerve cells in order to test for toxicity, the formation of macroscopic membranes was unexpectedly observed. Further study of EAK16 revealed that it has a β-sheet secondary structure and, in the presence of salt, forms membranes having unusual stability under various conditions. Observation of a β-sheet structure was surprising, since the sequence of EAK16 was predicted to form an α-helix (Chou and Fasman, 1978). Described below are the structure and properties of the membranes; peptides which are able to self-assemble into membranes; methods and conditions for producing the membranes; the ZUO1 gene and encoded zuotin, from which the EAK16 peptide sequence was derived; and uses of the macroscopic membranes.

Structure of the Macroscopic Membranes

The EAK16 peptide was observed to form a membranous structure with the appearance of a piece of transparent, thin (about 10–20 μm) plastic membrane when viewed under 100× magnification by phase-contrast microscopy. The membrane was formed in phosphate-buffered saline (PBS) and is colorless and isobuoyant.

The structure could also be observed with the naked eye by staining it bright red with Congo Red, a dye which preferentially stains β-sheet structures and is commonly used to visualize abnormal protein deposition in tissues (Pears, 1960).

At low magnifications (50–100×), the structure looks like a flat membrane. At high magnifications (30,000×) under a scanning electron microscope (SEM), structural details are revealed (FIGS. 3A–3H). The membranes in FIG. 3 were formed by adding EAK16 to PBS and prepared for SEM by incubating in 5% glutaraldehyde at 4° C. for 30 minutes, then dehydrated with ethanol and liquid $CO_2$. The photographs were taken at magnifications of 400, 800, 1600, 3000, 6000, 10000, 20000, and 30000× (FIG. 3A–H).

SEM revealed that the membrane is made up of individual filaments that are interwoven. The architecture of the structure appears to resemble high density felt or cloth. The diameter of the filaments are approximately 10–20 nm and the distance between the fibers are approximately 50–80 nm.

Figure 4:
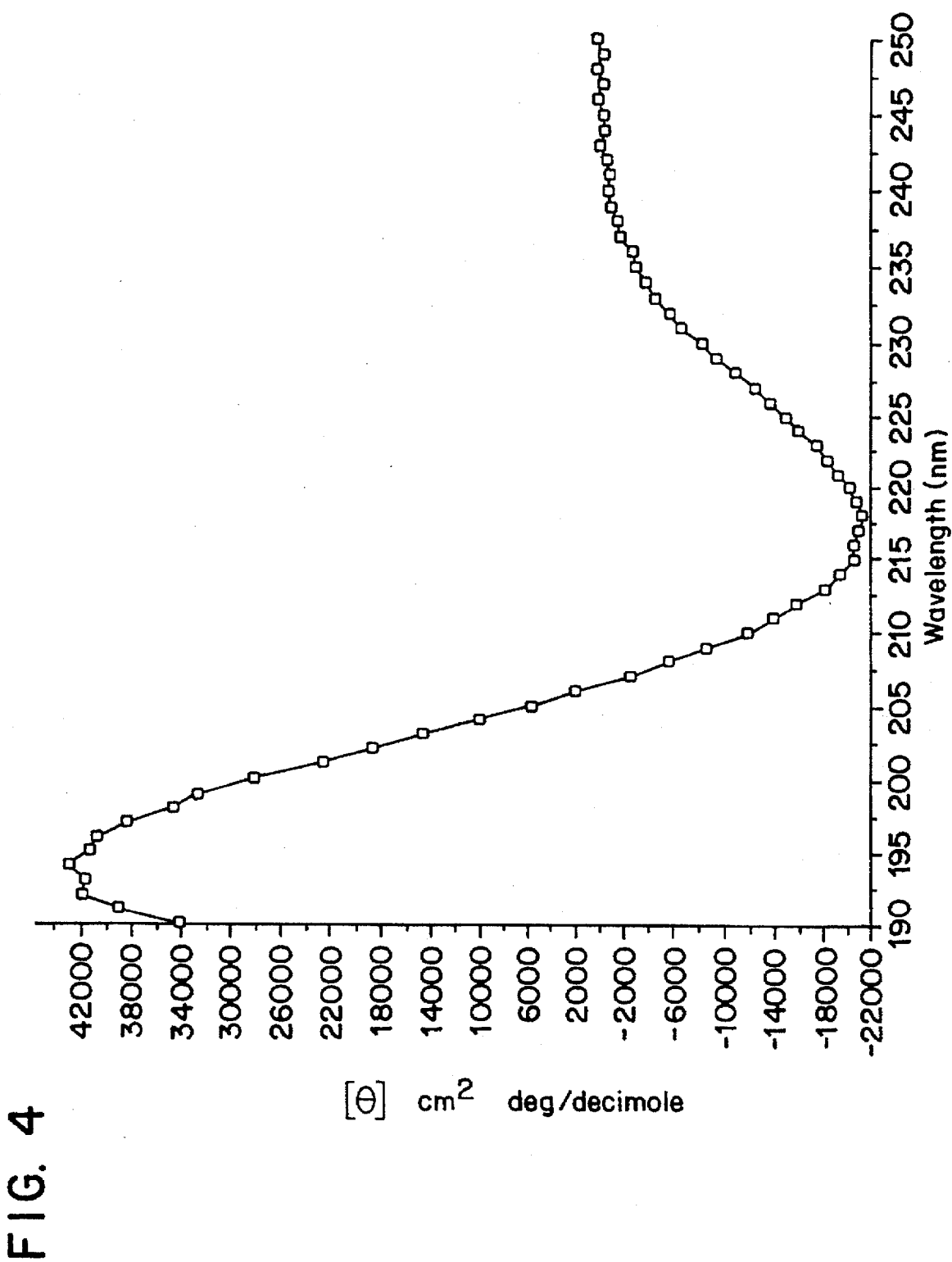
FIG. 4 is the typical β-sheet circular dichroism spectrum of the EAK16 peptide.

The β-sheet secondary structure of the membranes was confirmed by circular dichroism (CD) spectroscopy (FIG. 4). The EAK16 peptide was dissolved in water (10 μM) and the CD spectrum was taken. A typical β-sheet CD spectrum with an absorbance minimum at 218 nm and a maximum at 195 nm was detected. The β-sheet secondary structure of EAK16 was surprising, since a number of short peptides containing alanine, glutamic acid and lysine were previously reported to adopt stable α-helices in solution (Marqusee and Baldwin, 1987; Marqusee et al., 1989; Padmanabhan et al., 1991).

Length and Sequence of Membrane-forming Peptides

The effect of length and sequence on membrane formation was examined using several peptides (Table 1 and Example 3). The sixteen amino acid peptide, EAK16, with the sequence (AEAEAKAK)$_2$ (310-325 of SEQ ID NO:2), could undergo self-assembly, while twelve amino acid peptide, EAK12, with the sequence AEAKAEAEAKAK (SEQ ID NO:24), was able to associate to a much smaller extent and formed small and non-uniform pieces of membranous material. EAK8, AEAEAKAK (310-317 of SEQ ID NO:2), which has a single unit of the repeat, did not form membranes under identical conditions. Another 16 amino acid amphiphilic peptide, ARD16, having the sequence (ARARADAD)$_2$ (SEQ ID NO:3), was found to form macroscopic membranes. Its 8 amino acid counterpart, ARD8, did not form macroscopic membranes. These results indicate that peptide length is an important factor in the formation of macroscopic membranes. The peptide length should be more than 12 amino acids and preferably at least 16 residues. Very long peptides, e.g., of about 200 amino acids, may encounter problems due to insolubility and intramolecular interactions which destabilize membrane formation. Furthermore, peptides with a large amount of hydrophobic residues may have insolubility problems. The optimal lengths for membrane formation will probably vary with the amino acid composition.

Four non-amphiphilic peptides of varying amino acid sequence were tested for membrane formation; these are β-amyloid (1–28) (SEQ ID NO:4), β-amyloid (23–35) (SEQ ID NO:5), substance P (SEQ ID NO:6), and spantide (SEQ ID NO:7). None of these peptides produced macroscopic membranes under the identical conditions used with EAK16 and ARD16 (Table 1). These results indicate that the alternating hydrophobic and hydrophilic sequence of the peptide is important to membrane formation.

Figure 5A:
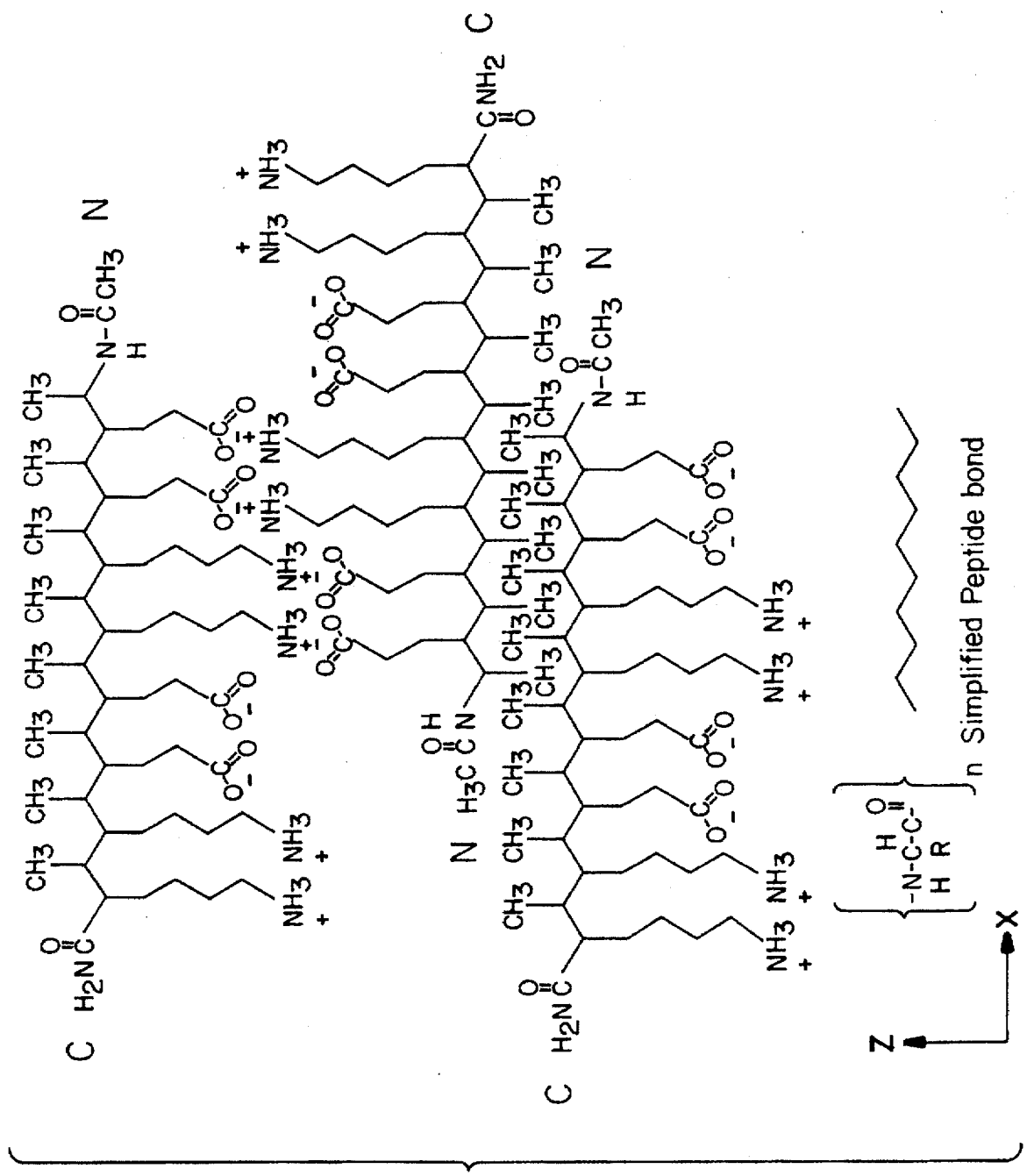
FIGS. 5A–5C show the hypothetical interactions between EAK16 molecules in the membranes and the secondary and tertiary structures resulting therefrom.

Consideration of these results leads to a hypothetical model in which intermolecular interactions between the peptides stabilize the secondary and tertiary structures of the membranes. Due to the alternating hydrophobic and hydrophilic residues of EAK16, β-sheets formed from EAK16 peptides can present a hydrophobic face and a hydrophilic face. The four glutamic acids of EAK16 have carboxyl side-chain groups with a pKa of 4.4–4.6 and the four lysines have amino side-chain groups with a pKa of 10.0–10.2. At neutral pH, the side-chains of the glutamic acids and lysines are negatively and positively charged, respectively. FIG. 5A shows the hypothetical interaction between three molecules of EAK16 peptide representing three antiparallel β-sheets. Two β-sheet layers are held together by hydrophobic interactions of alanine side-chains facing each other and two by ionized pair or salt bridge interactions between the charged lysines and glutamic acids facing each other. The structure can also be formed of parallel β-sheets. The tertiary structure comprising many β-sheets can be extended in the Z direction. In FIG. 5A, the peptides are staggered. The staggered arrangement allows extension of the structure in the X direction, along the peptide backbone.

Figure 5B:
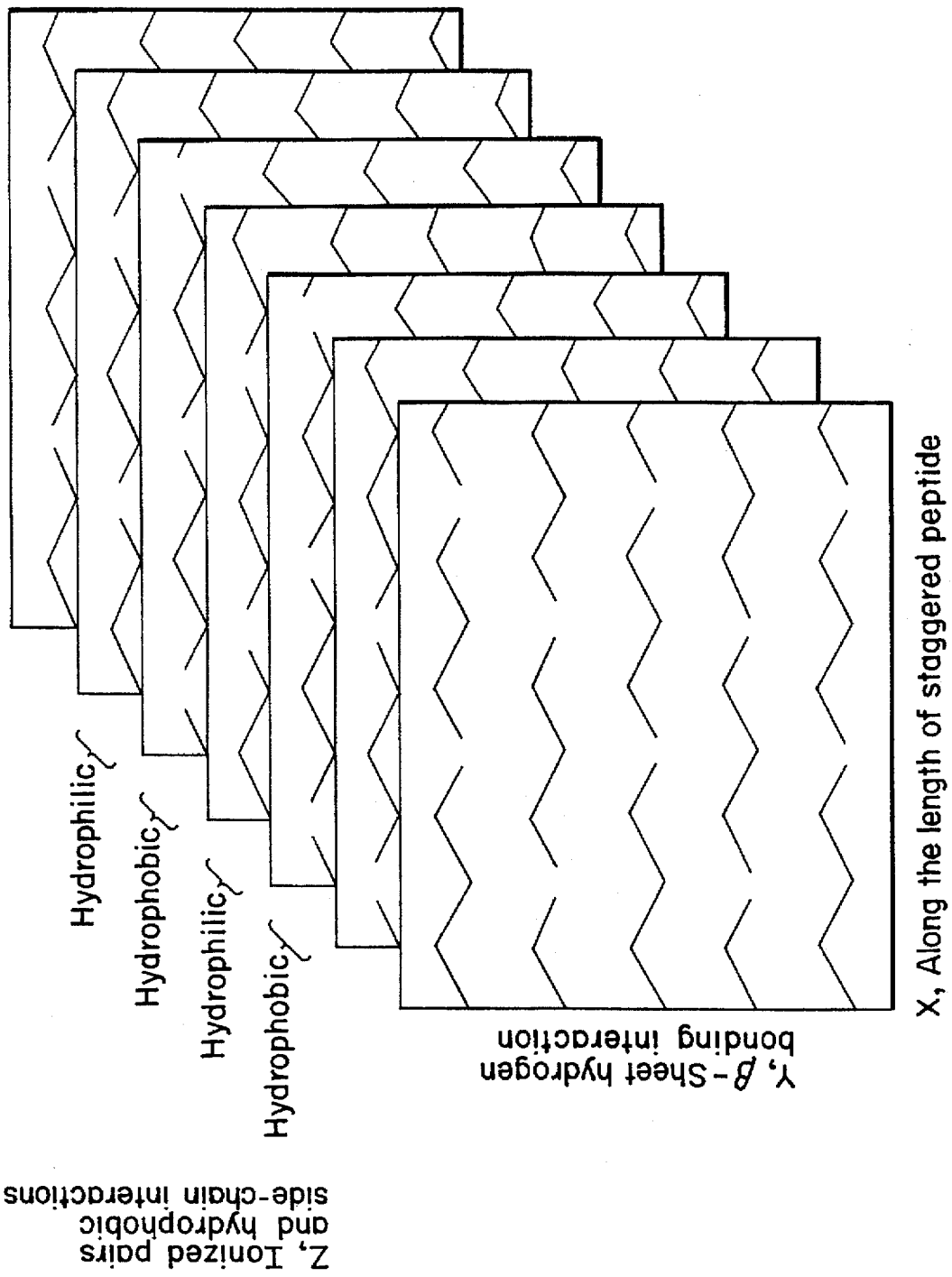

A three-dimensional view is shown in FIG. 5B. Each rectangle represents the plane of a β-sheet. In the Y dimension are the conventional β-sheet interactions, i.e., hydrogen bonding between the amino and carboxyl groups of the peptide backbones. In the X dimension, staggered coupling of the peptides within the β-sheets contributes to stability along the peptide backbone. In the Z dimension, interactions between β-sheets are stabilized by the extended ionized pair and hydrophobic interactions. The combination of these interactions are thought to result in the formation of β-barrel structures which may be the filaments observed under high magnification. The stagger distance between coupled peptides would determine the length of the filaments.

Figure 5C:
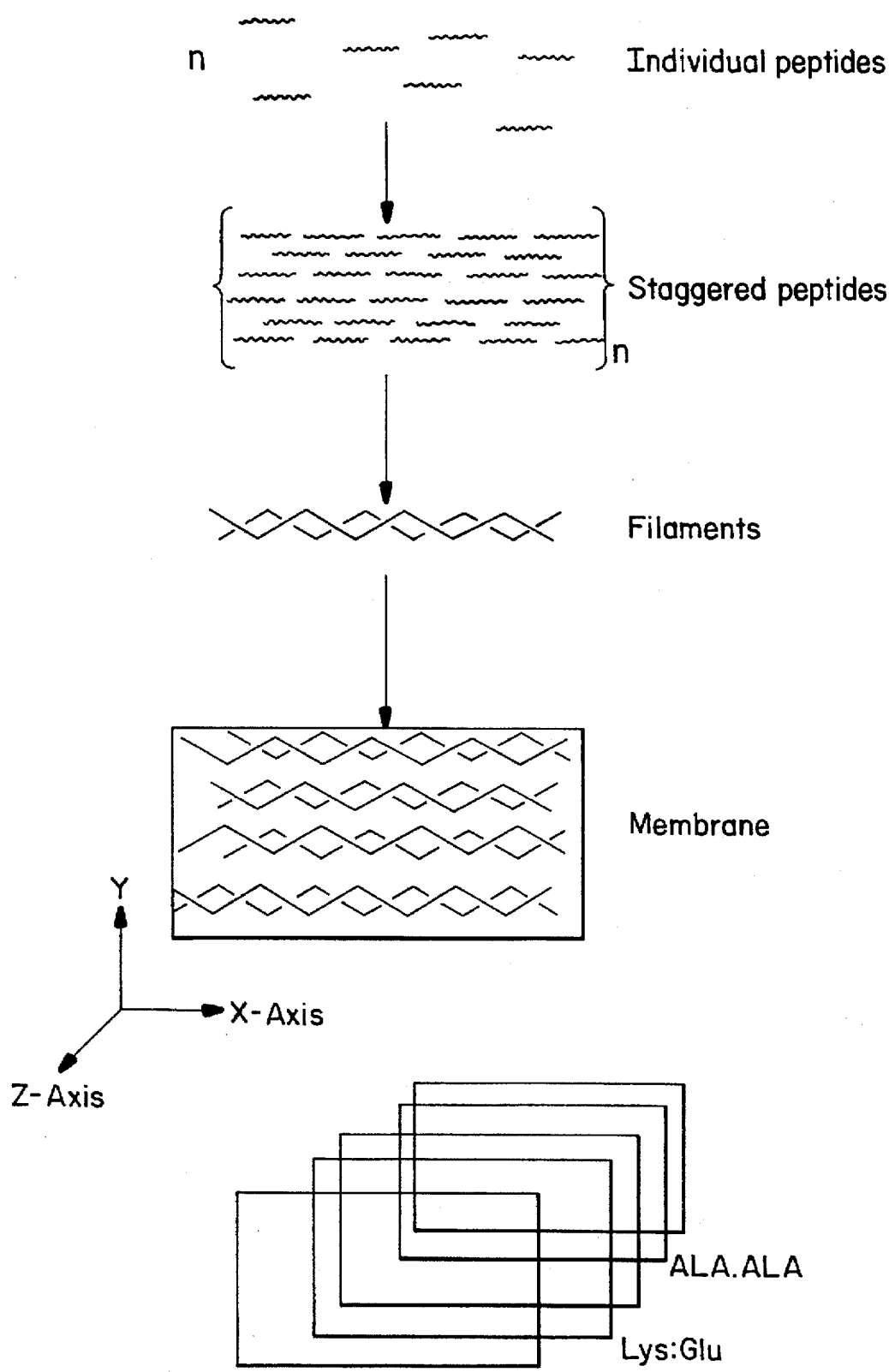

FIG. 5C illustrates the increasing levels of structural complexity as the peptides self-assemble into membranes.

Peptides which can form ionized pairs between their hydrophilic side-chains are referred to herein as complementary. Complementary pair interactions can also occur as a result of hydrogen bonding between the hydrophilic side-chains. Thus, Asn or Gln can function as hydrophilic amino acids in place of charged residues in membrane-forming peptides. Since ionized pair interactions are stronger than hydrogen bonds, peptides with acidic and/or basic amino acid side-chains would be expected to form more stable membranes than peptides with hydrogen bonding side-chains.

Figure 6A:
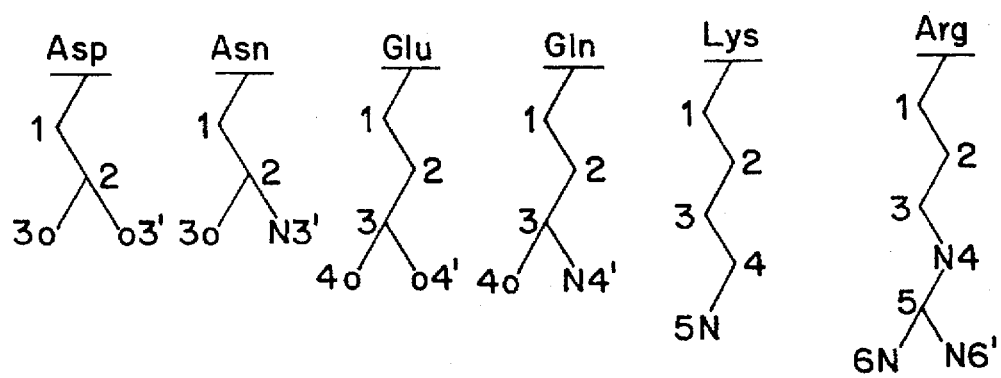
FIGS. 6A–6B illustrate calculation of the interpeptide distance of ionized and hydrogen bonding amino acid pairs.
Figure 6B:
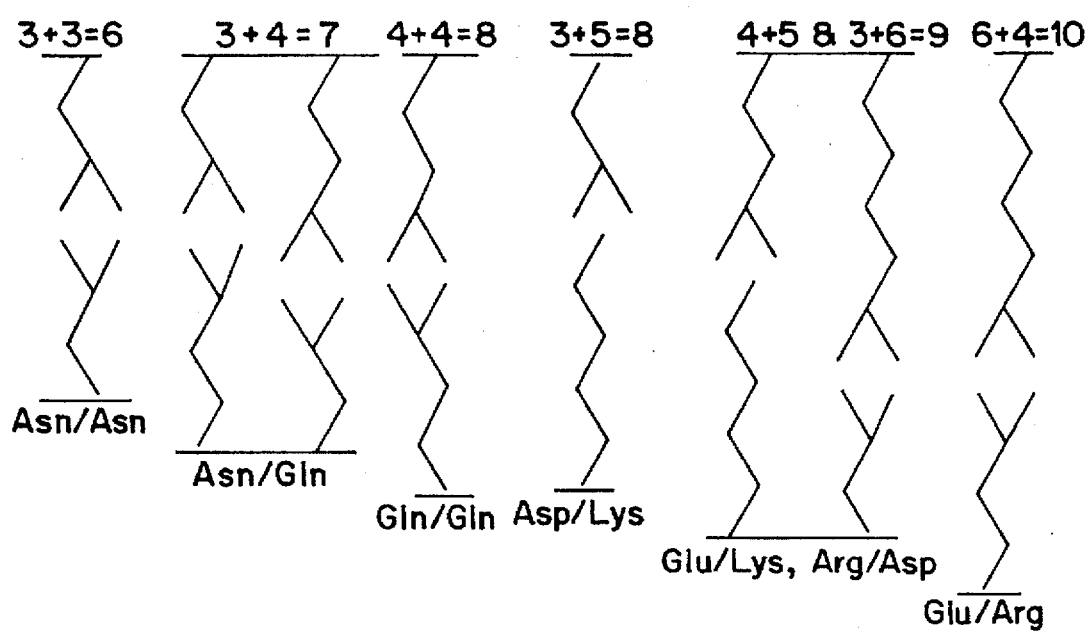

An additional stabilization factor is that complementary peptides maintain a constant distance between the peptide backbones. Peptides which can maintain a constant distance upon pairing are referred to herein as structurally compatible. The interpeptide distance can be calculated for each ionized or hydrogen bonding pair by taking the sum of the number of unbranched atoms on the side-chains of each amino acid in the pair (FIGS. 6A–6B). For example, lysine has 5 and glutamic acid has 4 unbranched atoms on its side-chains, respectively. An intermolecular interaction between two EAK16 peptides would involve ionized pairing between the lysine amino group and the glutamic acid carboxyl group. The interpeptide distance for a lysine-glutamic acid pair would be 5+4=9 atoms. Since all the pairs in a EAK16-EAK16 interaction would be Lys-Glu, the interpeptide distance would be constant at 9 atoms along the length of the peptides (FIG. 7A). Thus, the EAK16 peptide is self-complementary and self-compatible, and homogeneous mixtures of EAK16 form membranes.

FIG. 7A illustrates a convenient way to check whether two peptide molecules are complementary and structurally compatible. Various possibilities for staggering the coupling of the peptides are illustrated in FIG. 7B.

Amphiphilic peptides which are greater than 12 amino acids long, self-complementary and self-compatible, are expected to self-assemble into macroscopic membranes in homogeneous peptide solutions. Two examples, EAK16 and ARD16, have been demonstrated. Table 2 lists some other peptides which are predicted to form membranes in homogeneous mixtures. These examples illustrate some of the variety of amino acid arrangement and composition of membrane-forming peptides.

The criteria of amphilic sequence, length, complementarity and structural compatibility apply to heterogeneous mixtures of peptides. Suppose that two different peptides are used to form the membranes: peptide A, (SEQ ID NO:20), has Arg and Asp as the hydrophilic residues and peptide B, ADADAKAKADADAKAK (SEQ ID NO:21), has Lys and Asp (FIG. 7C). Peptides A and B are complementary; the Arg on A can form an ionized pair with the Asp on B and the Asp on A can form an ionized pair with the Lys on B. A calculation of the interpeptide distances in such pairs (FIGS. 6A–6B, however, shows that the two peptides are not structurally compatible. Using a conversion factor of 3Å per atom, the difference in interpeptide distance between the two pairs would be 3Å. Applicants estimate that a variation in interpeptide distance of more than 3–4Å would destabilize intermolecular interactions leading to membrane formation. Thus, in a heterogeneous mixture of peptides A and B, membranes would likely form, but they would be homogeneously composed of either peptide A or B.

Using this sort of calculation, it becomes evident that a peptide containing both Asn and Gln as hydrophilic residues will probably form membranes in which the peptides are staggered and Asn-Gln (interpeptide distance=7) pairs are formed, but not Asn-Asn (distance=6) and Gln-Gln (distance=8) pairs.

Membranes can also be formed of heterogeneous mixtures of peptides, each of which alone would not form membranes, if they are complementary and structurally compatible to each other. For example, mixtures of (Lys-Ala-Lys-Ala)$_4$ (SEQ ID NO:25) and (Glu-Ala-Glu-Ala)$_4$ (SEQ ID NO:26) or of (Lys-Ala-Lys-Ala)$_4$ and (Ala-Asp-Ala-Asp)$_4$ (SEQ ID NO:27) would be expected to form membranes, but not any of these peptides alone due to lack of complementarity.

Peptides, which are not perfectly complementary or structurally compatible, can be thought of as containing mismatches analogous to mismatched base pairs in the hybridization of nucleic acids. Peptides containing mismatches can form membranes if the disruptive force of the mismatched pair is dominated by the overall stability of the interpeptide interaction. Functionally, such peptides can also be considered as complementary or structurally compatible. For example, a mismatched amino acid pair may be tolerated if it is surrounded by several perfectly matched pairs on each side. Mismatched peptides can be tested for ability to self-assemble into macroscopic membranes using the methods described herein.

In summary, peptides expected to form macroscopic membranes have alternating hydrophobic and hydrophilic amino acids, are more than 12 amino acids and preferably at least 16 amino acids long, are complementary and structurally compatible. The hydrophobic amino acids include Ala, Val, Ile, Met, Phe, Tyr, Trp, Ser, Thr and Gly. The hydrophilic amino acids can be basic amino acids, e.g., Lys, Arg, His, Orn; acidic amino acids, e.g., Glu, Asp; or amino acids which form hydrogen bonds, e.g., Asn, Gln. Acidic and basic amino acids can be clustered on a peptide, as in EAK16 and ARD16. The carboxyl and amino groups of the terminal residues can be protected or not protected. Membranes can be formed in a homogeneous mixture of self-complementary and self-compatible peptides or in a heterogeneous mixture of peptides which are complementary and structurally compatible to each other. Peptides fitting the above criteria can self-assemble into macroscopic membranes under suitable conditions (described below).

The term peptides, as used herein, includes polypeptides and oligopeptides. The peptides can be chemically synthesized or they can be purified from natural and recombinant sources.

Formation of the Macroscopic Membranes

The novel self-assembly of EAK16 was initially observed in tissue culture medium (Dulbecco Modified Eagle's Medium, Gibco BRL, Gaithersburg, Md.) containing calf serum. Membranes can also form from EAK16 in phosphate-buffered saline (PBS: 150 mM NaCl, 10 mM sodium phosphate, pH 7.4). Macroscopic membranes do not form in water but appear after addition of sodium phosphate to a water-peptide solution to an approximate final concentration of 100 mg/ml. Thus, salt appears to play an important role in the self-assembly process.

Various metal cations were tested for effectiveness at inducing membrane formation from EAK16. The results indicate that monovalent metal cations induce membrane formation, but divalent cations primarily induce unstructured aggregates. Some anions, acetate, Cl$^-$, SO$_4^{-2}$ and PO$_4^{-2}$, and organic ions, NH$_4^+$ and Tris-Cl, were also tested and were not found to induce membrane formation.

The order of effectiveness of the monovalent cations appears to be Li$^+$>Na$^+$>K$^+$>Cs$^+$. Cs$^+$ produces the least amount of membranes and in addition, yields nonmembranous precipitates. The effectiveness of the monovalent cations appears to correlate inversely with the crystal radii of the ions: Li$^+$(0.6Å), Na$^+$ (0.95Å), K$^+$(1.33Å), and Cs$^+$ (1.69Å) (Pauling, 1960). A correlation is also seen with the hydrated radii of the ions: Li$^+$(3.4Å), Na$^+$(2.76Å), K$^+$(2.32Å), and Cs$^+$(2.28Å), and with the order of enthalpies of the monovalent cations (Pauling, 1960). It is not known at present if the monovalent metal cations act as a catalyst or if they are incorporated into the membrane. The size of the filaments (10–20 nm) and interfilament distance (50–80 nm) in the membranes formed from EAK16 suggest that hydrated ions may stabilize the intermolecular interaction.

Concentrations of monovalent metal cations (NaCl) as low as 5 mM and as high as 5M have been found to induce membrane formation within a few minutes. Thus, membrane formation appears to be independent of salt concentration over this wide range. Salt concentrations of less than 5 mM may also induce membrane formation, but at a slower rate.

The initial concentration of the peptide is a significant factor in the size and thickness of the membrane formed. In general, the higher the peptide concentration, the higher the extent of membrane formation. Membranes can form from initial peptide concentrations as low as 0.5 mM or 1 mg/ml. However, membranes formed at higher initial peptide concentrations (about 10 mg/ml) are thicker and thus, likely to be stronger. Therefore, it is preferable when producing the membranes to add peptide to a salt solution, rather than to add salt to a peptide solution.

Formation of the membranes is very fast, on the order of a few minutes, and seems to be irreversible (see below). The process is unaffected by pH$\leq$12 (the peptides tend to precipitate out at pH above 12), and by temperature. The membranes can form at temperatures in the range of 4° to 90° C.

Formation of the membranes is inhibited by the presence of divalent metal cations at concentrations equal to or greater than 100 µM, which promote unstructured aggregation rather than membrane formation, and by sodium dodecyl sulfate (SDS) at a concentration of at least 0.1%.

Properties of the Macroscopic Membranes

Once formed, the macroscopic membranes are stable in a variety of aqueous solutions, including water, phosphate-buffered saline (PBS), tissue culture medium, serum, and also in ethanol, and can be transferred to and stored in any of these liquids. Membranes formed of EAK16 and ARD16 have been found to be stable in water or PBS for at least a week without any sign of deterioration. The membranes can be transferred from one solution to another using a solid support such as a spatula. They can be broken by cutting, tearing or shearing.

Membranes formed of EAK16 were found to be unusually stable under various conditions expected to disrupt them. Circular dichroism (CD) spectroscopy measurements further demonstrated the unusual stability of the β-sheet secondary structure of the peptide EAK16 (Example 4). The β-sheets can be thought of as the building blocks for the macroscopic membrane structures and their unusual stability confirms the strength of the peptide interactions holding the membrane together.

Figure 8A:
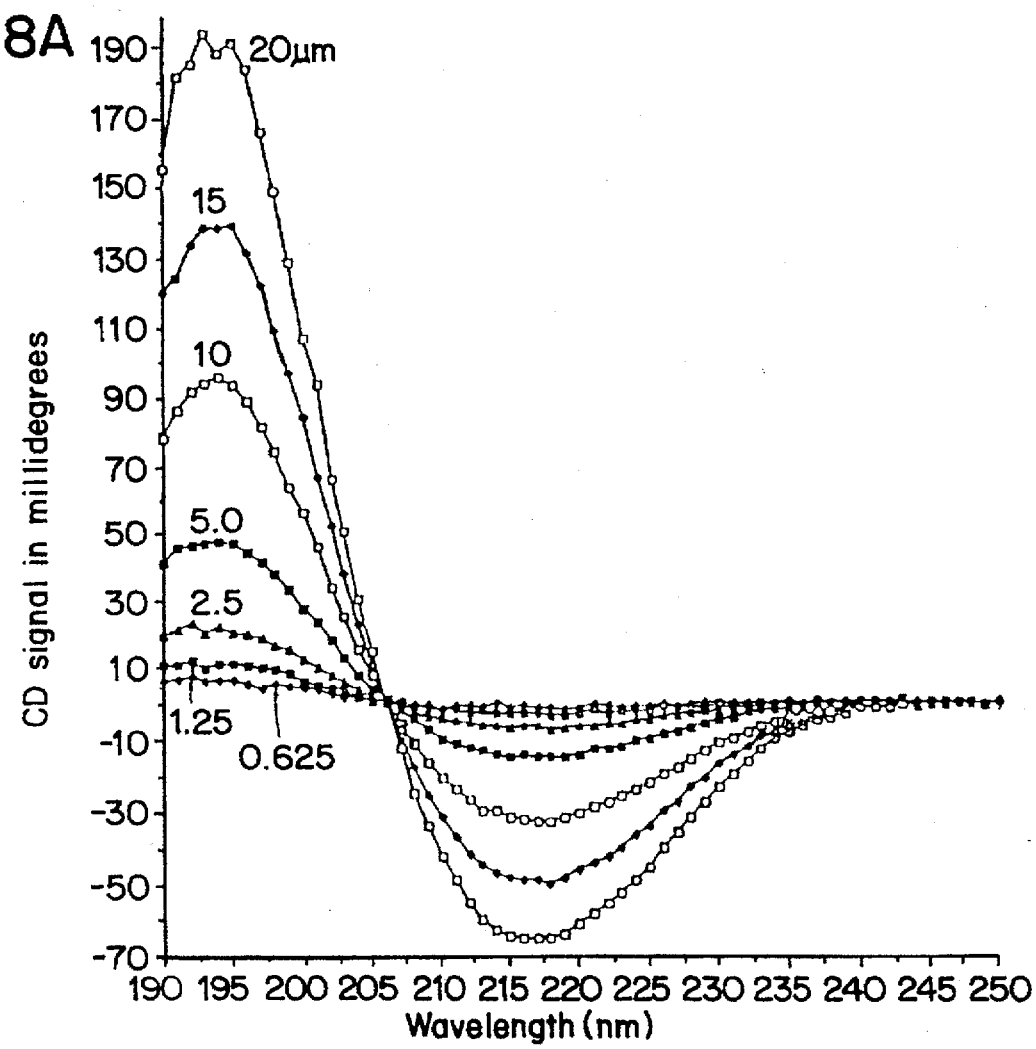
FIGS. 8A and 8B show the stability of the β-sheet structure of peptide EAK16 in water at different peptide concentrations.
Figure 8B:
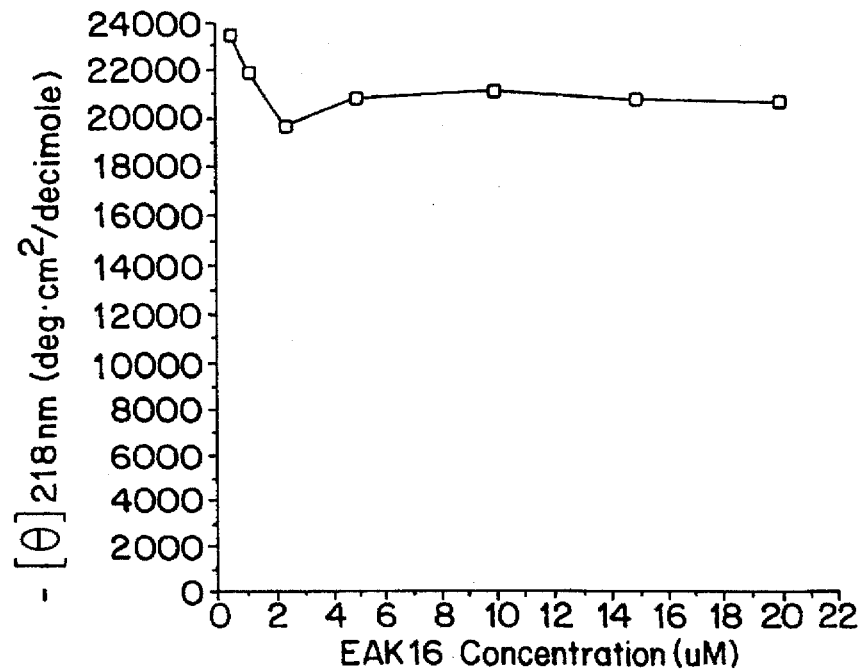

The β-sheet structure of EAK16 was not significantly affected by dilution of the peptide, as seen in FIGS. 8A and 8B. FIG. 8A shows the CD spectra of EAK16 at 0.625, 1.25, 2.5, 5.0, 10, 15 and 20 µM peptide concentrations in water. The Y axis is expressed as CD signal in millidegrees in order to show the β-sheet stability of the peptide in diluted concentrations. These data show that, even at the lowest concentration (0.625 µM), the characteristic β-sheet CD spectrum with minimum at 217 nm and maximum at 194 nm was still clearly recorded. The CD signal is linearly proportional to the peptide concentration, suggesting that the β-sheet structure is stable in very dilute concentrations. Note that the spectra cross an isosbectic point at 205 nm, thus, indicating that the same structures exist at all the peptide concentrations. FIG. 8B shows a plot of normalized peptide concentrations from 0.625 to 20 µM vs. the mean residue ellipticity at 218 nm. The stability of the β-sheet structure of EAK16 at very dilute concentrations of the peptide contrasts with observations of other β-sheet forming peptides, such as β(29–42) and β(1–42) of the β-amyloid protein (Barrow and Zagorski, 1991) and the TL-LRR1 peptide (23 residue length) from the toll protein of Drosophila (Gay et al., 1991), which show a stable β-sheet only in high peptide concentrations.

The stability of the membranes was also tested under a range of temperature, pH and chemical conditions. For these experiments, membranes were formed by adding 20 µl of a 0.5 mM stock solution of EAK16 to 0.5 ml of PBS, and transferred into water or other solutions at test conditions.

Figure 9A:
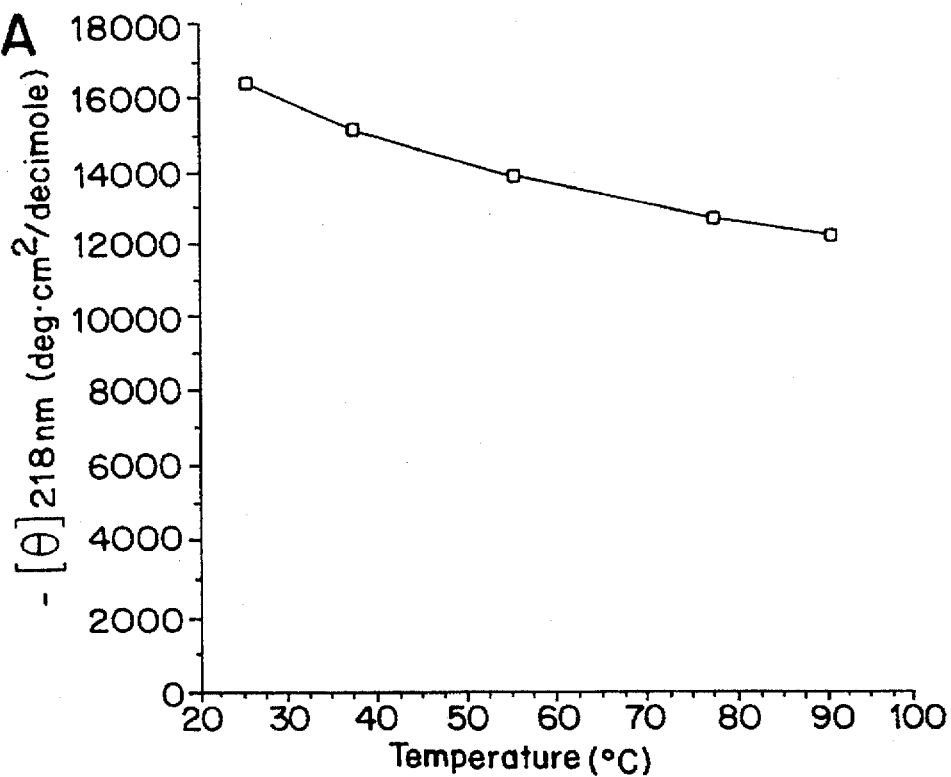
FIGS. 9A and 9B show the thermal stability of the β-sheet structure of EAK16.
Figure 9B:
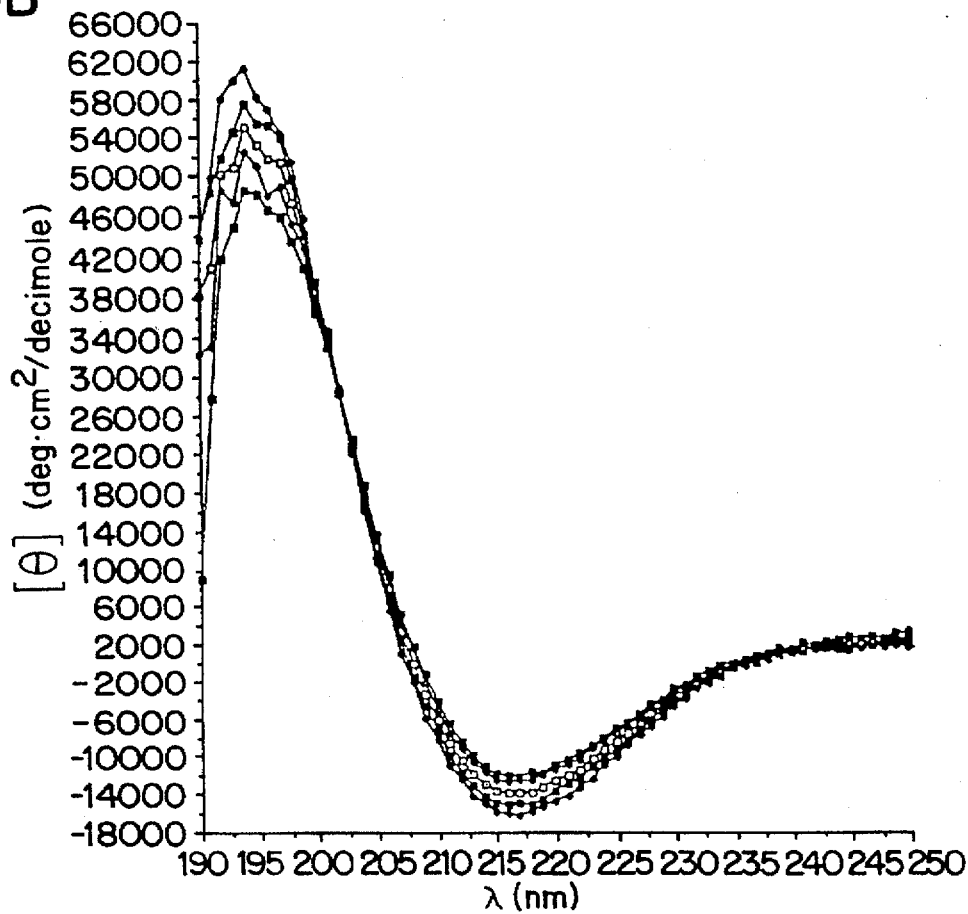

The membranes were found to be stable in water over a wide range of temperatures: up to 95° and at 4°, –20°, and –80° C. The membranes could be frozen and thawed, although care was required in handling the frozen membranes which were brittle. In boiling water, the membranes tended to be sheared by the mechanical agitation. The CD spectra of EAK16 were also found to be unaffected over the range of 25°–90° C. (FIGS. 9A and 9B). FIG. 9B shows the CD spectra of EAK16 (8 µM) at 25°, 37°, 55°, 70° and 90° C. The thermal profile of EAK16 (FIG. 9A) shows a 22% decrease of mean residue ellipticity over this range. Such strong thermal stability of the defined β-sheet structure of EAK16 is unusual for a small peptide. For example, these findings contrast with the α-helix-forming sixteen residue (Ala, Glu, Lys)-containing peptides studied previously (Marqusee and Baldwin, 1987).

The EAK16 membranes were also tested in water at pH 1.5, 3, 7 and 11 at room temperature for at least a week and at 95° C. for about 4 hours. The membranes were unaffected at these pH. The β-sheet structure of the peptide was also unaffected over this pH range; the pH profile (FIG. 10) shows a less than 10% decrease of ellipticity. Precipitation of the peptide was observed at pH above 12.5. These findings suggest that the overall β-sheet structure of EAK16 is not altered drastically in various pH even though charged residues would be neutralized under such conditions. It is possible that the complementary interactions between the Glu and Lys side-chains are strong even when the carboxyl groups of the Glu residues have been protonated at pH 1.5 and 3, due to their ability to form hydrogen bonds even when protonated.

The EAK16 membranes were further tested for resistance to chemical denaturation under the following conditions: 1% and 10% sodium dodecyl sulfate (SDS); 1, 2, 3, 4, 5, 6 and 7M guanidine-HCl; and 1, 2, 3, 4, 5, 6, 7 and 8M urea. The membranes remained stable in the presence of these chemicals at room temperature for at least 4 days. The membranes were also tested at 95° C. for 4 hours in 10% SDS; 7M guanidine-HCl; and at 8M urea. At this temperature, the membranes dissolved in 8M urea, but remained intact in SDS and 7M guanidine-HCl.

Figure 11:
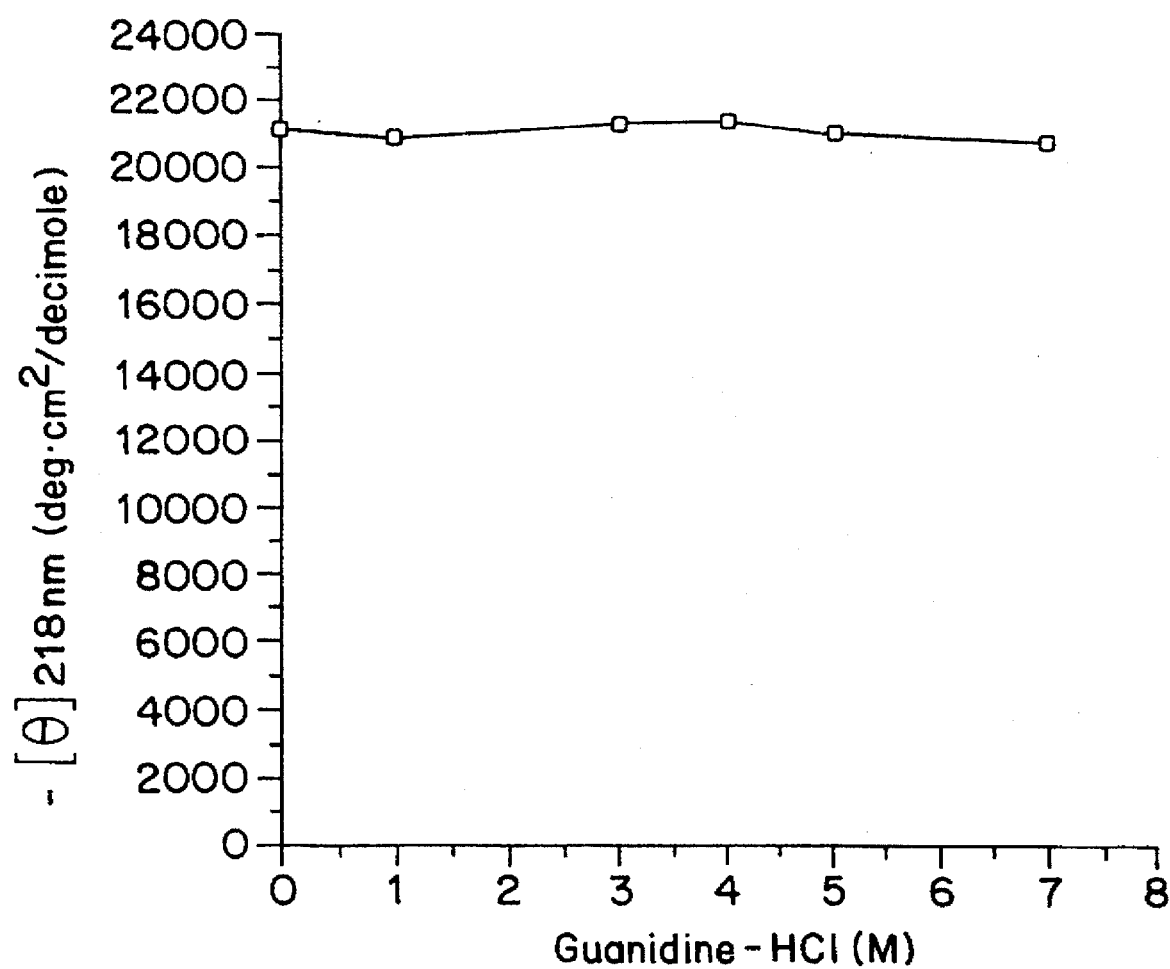
FIG. 11 shows the stability of the β-sheet structure of EAK16 in guanidine-HCl.

CD spectra measurements also showed that the β-sheet structure of EAK16 was not significantly affected by incubation in 0.1% SDS at 90° C., 1–7M guanidine-HCl at room temperature or 8M urea at room temperature for over 16 hours. No significant differences in CD signals were observed even under the strongest denaturing conditions of 7M guanidine-HCl (FIG. 11) and 8M urea. This is surprising, since 7M guanidine-HCl and 8M urea can effectively denature most proteins and proteinaceous aggregates, including other β-sheet forming peptides (Trudelle, 1975). Furthermore, these denaturants are expected to diminish hydrogen bonds and hydrophobic interactions. The stability of the EAK16 secondary structure suggests that the peptide molecules strongly interact to form an interwound β-sheet structure. This is consistent with the interwound filamentous structures observed in the presence of monovalent alkali salts.

The peculiar stability of the secondary and tertiary structure of EAK16 observed may be explained by the additive stabilizing interactions illustrated by FIG. 5. It is known from theoretical calculations that each ionic bond can contribute approximately 5 Kcal/M and that the interaction of apolar side-chains of alanines can contribute 1 Kcal/M. The hydrogen bonds between C=O and the N in the backbone of peptides can also contribute approximately 3 Kcal/M. Therefore, EAK16 would have a total interaction energy of about 72 Kcal/M per two molecules. Since the β-sheets are staggered and overlayed, the additive interaction energy is much greater than that of individual molecules. The peptide bond itself has only 5–7 Kcal/M and is very stable. In addition, the hydrophobic and hydrophilic interactions between β-sheets seem to stabilize the secondary structure under conditions in which β-sheets are usually disrupted. Thus, it appears that even under very harsh conditions, the stabilization energy of these membrane-forming peptides is greater than the disruption energy.

It is interesting to note that the EAK8 and EAK12 peptides do not have such unusual stability. EAK8 exhibited a random coil structure under identical conditions. EAK12 was found to denature from a β-sheet structure at high temperatures, and to subsequently undergo reversible helix-coil transitions. This is consistent with our model, in which stabilization in the direction of the peptide backbone (X dimension, FIG. 5) is also significant.

Further analysis by methods such as fiber X-ray diffraction and atomic force microscopy may provide more insights into the organization and stabilization of the membrane structure.

The membranes also have some interesting and useful biological properties. They are highly resistant to digestion by proteases. Membranes formed from EAK16 were not degraded by trypsin, α-chymotrypsin, papain, protease K, or pronase at 100 μg/ml concentration in the appropriate buffers when incubated at 37° C. overnight or at room temperature (25° C.) for a week, even though the EAK16 peptide contains potential protease cleavage sites.

The membranes also appear to be non-cytotoxic. The EAK16 peptide formed macroscopic membranes when added to a tissue culture of nerve growth factor-differentiated rat PC12 cells. The peptides and resultant membranes did not affect the appearance or rate of growth of the cells.

Uses of the Macroscopic Membranes

The above-described macroscopic membranes have several uses. Because they are stable in serum, resistant to proteolytic digestion and alkaline and acidic pH, and are non-cytotoxic, these membranes are potentially useful in biomaterial applications, such as medical products (e.g., sutures), artificial skin or internal linings, and slow-diffusion drug delivery systems. The membranes can be made and stored in a sterile condition. For example, they can be produced using synthetic peptides and sterile PBS and stored in sterile PBS. The membranes can also be stored in a water/ethanol solution. In addition, the membranes have a simple composition and can be easily and relatively inexpensively produced in large quantities. They can be used in numerous applications in which permeable and water insoluble material are appropriate, such as separation matrices (e.g., dialysis membranes, chromatographic columns).

Due to their permeability, the membranes described herein are potentially useful as slow-diffusion drug delivery vehicles for protein-type drugs, including erythropoietin, tissue type plasminogen activator, synthetic hemoglobin and insulin. The drug could be wrapped in layers of membrane, which would permit slow release of the drug and may extend the half-life of the drug in the bloodstream. Because the membranes are resistant to degradation by proteases and stomach acid (pH 1.5), drug delivery vehicles made of these membranes could be taken orally.

The extremely small pore size of the membranes may make them useful as filters, for example, to remove virus and other microscopic contaminants (see e.g., Erickson, 1992). The pore size (interfilament distance) and diameter of the filaments in the membranes can be varied by varying the length and sequence of the peptides used to form the membranes.

Modification of the membranes may give them additional properties. For example, the membranes may be further strengthened by cross-linking the peptides after membrane formation by standard methods. Collagen may be combined with the peptides to produce membranes more suitable for use as artificial skin; the collagen may be stabilized from proteolytic digestion within the membrane. Furthermore, combining phospholipids with the peptides may produce vesicles.

The membranes may also be useful for culturing cell monolayers. Cells prefer to adhere to non-uniform, charged surfaces. The charged residues and conformation of the proteinaceous membranes are likely to promote cell adhesion and migration. In fact, cells were observed to adhere to EAK16 membranes floating in the tissue culture dish. In addition, the permeability of the membranes would permit diffusion of small molecules, such as growth factors or peptide hormones, to the underside of cell monolayers, thus, presenting the potential for tissue culture of differentiated cells and/or stratified cell layers.

The filamentous structure of the membranes described herein is similar to the structure of silk fibroin protein, which consists largely of glycine-alanine/serine or alanine-glutamine repeats and forms stable β-sheet filaments, although the silk fibroin protein has a molecular weight greater than 360,000 (Lizardi, 1979), whereas EAK16 has a molecular weight of only 1,760. The filaments formed by EAK16 are much finer than silk fibers. The membranes formed by EAK16 and other amphiphilic peptides described herein may be useful for making very thin, transparent fabric.

In addition, it is interesting that the neurofibrillary tangles and amyloid plaques associated with neuropathological conditions, such as Alzheimer's disease, are salt-dependent aggregates of β-amyloid protein with extremely stable and highly insoluble β-sheet structure (Iqbal and Wisniewski, 1983). The aggregated Alzheimer's filament has a diameter of approximately 10–15 nm (Hilbich et al., 1991; Iqbal and Wisniewski, 1983; Halverson et al., 1990; Kirschner et al., 1987), similar to the dimensions of the EAK16 peptide filaments. Ordered filamentous aggregates (approximately 7–10 nm in diameter) have also been reported in another β-sheet forming peptide, TL-RR1, a 23 amino acid peptide segment found in the Drosophila Toll protein (Gay et al., 1991). Moreover, the scrapie prion protein also stains with Congo Red and forms aggregated filaments which are extremely stable and resistant to proteases. Thus, the formation of the macroscopic membranes may provide a useful model system for investigating the properties of biological proteins structures with such unusual properties as extreme insolubility and resistance to proteolytic digestion. Studies in such a model system may provide insights into the pathology and potential treatment of conditions characterized by the presence of these proteins or proteinaceous structures. For example, drugs which inhibit the self-assembly of the EAK16 peptide or other membrane-forming peptide into filaments or filamentous membranes can be identified. Drugs identified by such a method may be useful for treating Alzheimer's disease or scrapie infection.

In addition, the ability of small peptides such as EAK16 to self-assemble into membranes may be useful in origin of life studies related to cell membranes and cellular compartmentalization. Apropos to this sort of investigation is the interesting observation that the EAK16 peptide shows partial nucleotide hydrolysis activity. This activity is probably due to the ability of lysine and glutamic acid side-chains to perform general acid and base catalysis.

Zuotin

The sequence of EAK16 was originally found in a yeast protein called zuotin. Zuotin was identified by its ability to bind preferentially to left-handed Z DNA in a gel shift assay developed by Applicants. The zuotin gene, ZUO1, was cloned and sequenced (SEQ ID NO:2). ZUO1 was found to encode a 433 amino acid protein having several interesting features. In addition to the alternating alanine and charged residues of the EAK16 sequence, the protein contains several potential phosphorylation sites (FIG. 1), including sites recognized by the CDC28 (or cdc2) kinase (✱), casein kinase II (O), cAMP-dependent protein kinase (▼), tyrosine kinase (★), and protein kinase C (●). Zuotin also contains a bipartite nuclear targeting sequence.

Two distinct regions of zuotin were found to be similar to known proteins. One region (residues 111–165) was similar to E. coli DnaJ, yeast YDJ1, yeast SCJ1, yeast SIS1, SEC63 (or NLS1), avian polyomavirus small t and large T antigens, Drosophila csp29 and csp32, and human HDJ-1. A second region (residues 300–363) of zuotin is similar to several histone H1 variants, including some human, chicken and sea urchin variants.

Both partially purified yeast zuotin and bacterially expressed recombinant zuotin exhibited a high affinity for DNA in the left-handed Z conformation. The region of zuotin from amino acids 306 to 339 (heavily underlined in FIG. 1) is thought to be the DNA-binding domain. Mutational analysis showed that ZUO1 is not an essential gene, but that disruption of its function leads to slow cell growth.

The partial purification of the putative Z-DNA binding protein from yeast S. cerevisiae, the cloning and characterization of its gene and functional analysis are further described in Example 5.

The following examples illustrate the invention further and more specifically.

EXAMPLE 1

PEPTIDE SYNTHESIS, PURIFICATION, AND SOLUBILITY

The peptides were synthesized by solid-phase peptide synthesis on an Applied Biosystems Model 430A peptide synthesizer coupler using standard N-tert-butyoxycarbonyl (t-Boc) chemistry and cycles using n-methylpyrolidone (NMP) chemistry (Steward and Young, 1984). Both N- and C-termini of the peptide EAK16 were blocked to resemble its native state in the protein zuotin. The C-terminal amides were synthesized on p-methylbenzhydrylamine resin and the N-terminus of the peptide was acetylated using acetic acid anhydride with an equivalent of diidopropylethylamine (DIEA) in dimethylformamide. The peptides were cleaved from the resin using hydrofluoric acid/anisole 10:1 (v/v) (Applied Biosystems, 1986).

The peptides were purified through HPLC (high pressure liquid chromatography) using a Vydac $C_{18}$ semi-preparative column, eluted with a gradient of 5–60% acetonitrile in 0.1% trifluoroacetic acid (TFA), and lyophilized in a speed vacuum. Peptide purity was determined by analytic HPLC and the composition was determined by amino acid analysis.

Peptide stock solutions were prepared at a concentration of approximately 0.57 mM (1 mg/ml) in water. The molecular weight of EAK16 is 1,760. EAK16 has a maximal solubility of 3 mM (about 5 mg/ml) in water, but can be solubilized at up to 6 mM (about 10 mg/ml) in 23% acetonitrile. The concentration was determined by the ninhydrin methods using internal controls.

EXAMPLE 2

CIRCULAR DICHROISM MEASUREMENT

Circular dichroism (CD) spectra were taken on an Aviv Model 60DS spectropolarimeter using program 60HDS for data processing. Because EAK16 contains both positively and negatively charged residues, the peptide itself can serve as a buffer. CD samples were prepared and measured at 25° C., unless otherwise indicated. All reagents were ultrapure and solutions were filtered through a 0.22 μM pore filter before use.

EXAMPLE 3

PREPARATION AND TESTING OF PEPTIDES FOR MEMBRANE FORMATION

The EAK16, EAK12, and EAK8 peptides were synthesized by a peptide synthesizer (Applied Biosystems) and purified by reverse phase HPLC and eluted by a linear gradient of 5–80% acetonitrile, 0.1% TFA. The concentration of the peptides was determined by dissolving dried peptide in solution (w/v) and centrifuging the solution. Then, a portion of the solution was analyzed by hydrolysis with internal controls. The sequence of the peptides were confirmed by microsequencing (Edman degradation) using the Applied Biosystems peptide sequencer (Steward and Young, 1984; Applied Biosystems, 1986). The compositions of the peptides were confirmed by hydrolytic analysis.

Substance P, Spantide, and β-amyloid (1–28) are available from Bachem. β-amyloid (1–28) was also described in Barrow and Zagorski (1991). Substance P, Spantide, and β-amyloid (25–35) were aminylated on the C-terminal ends.

The EAK12 and EAK16 tested for membrane formation were acetylated and aminylated at both N- and C-terminal ends. Blocking of both of the N- and C-termini of EAK16 appeared not to be essential for membrane formation. The peptides were initially dissolved in water (5 mg/ml) or in 23% acetonitrile (10 mg/ml). A volume of 5–10 microliters of the dissolved peptides were applied to the DMEM medium, PBS or water. The formation of the membrane was first observed under a phase-contrast microscope and then, by the naked eye after staining with Congo Red.

EXAMPLE 4

STABILITY OF THE β-SHEET STRUCTURE OF EAK16

Circular dichroism (CD) spectroscopy was used to monitor the stability of the μ-sheet structure of EAK16 under various conditions.

Dilute peptide concentrations. EAK16 secondary structure was found to be stable in very dilute concentrations of the peptide. A 3 mM stock EAK16 solution was mixed in water to a concentration of 20 μM, allowed to equilibrate, and the CD spectrum measured. The solution was then diluted five times by two-fold serial dilutions to final concentrations of 15, 10, 5.0, 2.5 and 0.625 μM, allowed to equilibrate and CD spectra taken. Reverse experiments, in which the concentration of peptide was increased by adding more peptide, were also done and similar results were obtained.

Figure 10:
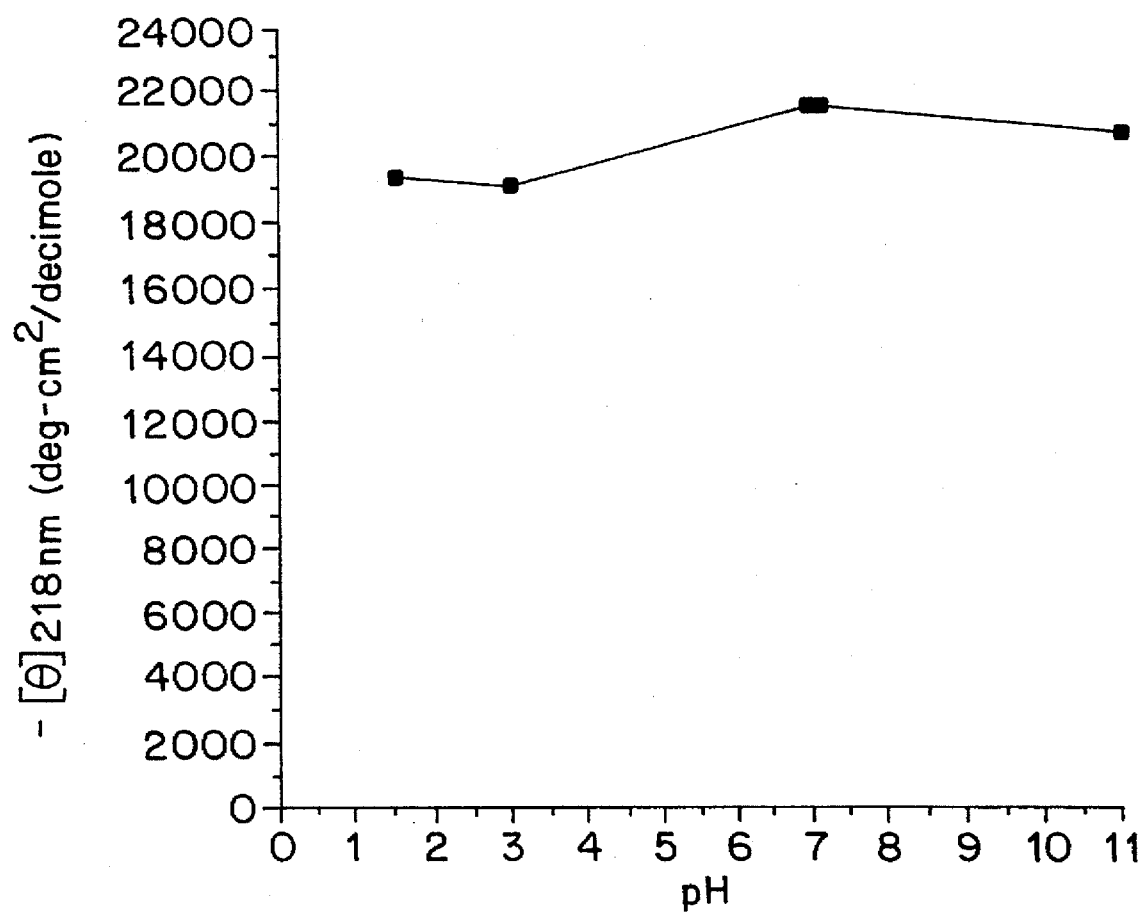
FIG. 10 shows the stability of the β-sheet structure of EAK16 at different pH.

Temperature. The CD spectra of 8 μM EAK16 at 25°, 37°, 55°, 70° and 90° C. in water were measured. The ratios of ellipticity at 194 nm/217 nm remained approximately 4.0 over the temperature range of 25°–90° C. (Table 3); such a high ratio suggests strong stability of the β-sheet structure. The secondary structure of EAK16 was not substantially altered over this range of temperature and an isosbectic point was observed at 202 nm. The thermal profile showed a 22% decrease of $-[\theta]_{218\ nm}$ deg. cm$^2$/decimole (FIG. 9).

pH. The β-sheet structure of EAK16 was also not significantly affected by pH. The peptide consists of 4 positively charged lysine and 4 negatively charged glutamic acid residues at neutral pH. Lysine has a calculated pKa of 10.0 and glutamic acid has a pKa of 4.4 in proteins. EAK16 has a calculated pI of 6.71. It was assumed that changes of pH would have a great effect on the β-sheet structure, especially when the charged groups are neutralized. However, CD spectra of EAK16 showed that pH had little effect on the secondary structure over a pH range of 1.5 to 11 (FIG. 10). The 3 mM stock solution of EAK16 was mixed with pH buffers at pH 1.5, 3, 7, and 11 to a final concentration of 10 μM and allowed to equilibrate for 4 hours before taking CD measurements. Insignificant differences in ellipticity were observed at these pH. The pH profile showed a less than 10% decrease of $-[\theta]_{218\ nm}$ deg. cm$^2$/decimole from pH 1.5 to 3, 7 and 11 (FIG. 10). However, when pH was increased beyond 12.5, precipitation of the peptide was observed.

Chemical denaturants. CD spectra measurements also showed that the β-sheet structure of EAK16 was not significantly affected by incubation in SDS (1% at 90° C.), 7 M guanidine-HCl or 8M urea for over 16 hours. The peptide (3 mM stock) was mixed with water or different concentrations of guanidine-HCl or urea and allowed to incubate overnight before taking CD measurements. SDS was added to a peptide solution to a final concentration of 0.1% and incubated for 30 minutes. No significant differences in CD signals were observed even under the strongest denaturing conditions of 7M guanidine-HCl (FIG. 11) and 8M urea.

EXAMPLE 5

IDENTIFICATION, CLONING AND CHARACTERIZATION OF THE YEAST PROTEIN ZUOTIN

INTRODUCTION

DNA is capable of undergoing a number of conformational changes; the most dramatic of these is from right-handed B-DNA to left-handed Z-DNA. There are several conditions that are known to stabilize Z-DNA. For example, poly(dG-m$^5$dC) converts readily to left-handed Z-DNA in vitro in the presence of millimolar concentrations of divalent metals and polyamines, as well as small peptides (Behe and Felsenfeld, 1981: Rich et al., 1984; Takeuchi et al., 1991). Certain DNA sequences, especially alternating purines and pyrimidines can adopt the Z-conformation in response to negative supercoiling (Peck et al., 1982). Inside the cell, negative supercoiling can be generated during transcription (Liu and Wang, 1987; Tsao et al., 1989). Furthermore, the equilibrium between B- and Z-DNA can be influenced by proteins that preferentially bind one of the two conformations (Lafer et al., 1985).

A number of studies suggests that Z-DNA may exist in vivo (Jaworski et al., 1987; Rahmouni and Wells, 1989; Wittig et al., 1989); however, the extent of its occurrence is yet to be determined. Z-DNA has been implicated in some important biological processes, such as general DNA recombination (Bullock et al., 1986; Treco and Arnheim, 1986; Blaho and Wells, 1987; Wahls et al., 1990), and both positive and negative transcriptional regulation (Nordheim and Rich, 1983; Naylor and Clark, 1990).

RESULTS

Detection of a Poly(dG-m$^5$dC) Binding Protein in *S. cerevisiae*

Two probes that can be stabilized in the Z-form were used to detect potential Z-DNA binding proteins. One is an ~600 bp fragment of $^{32}$P-labelled poly(dG-m$^5$dC) that is stabilized in the Z-DNA form by millimolar concentrations of MgCl$_2$ (Behe and Felsenfeld, 1981); the other is an oligonucleotide, [$^{32}$P](dG-BR$^5$dC)$_{22}$, that can be stabilized by millimolar concentrations of MgCl$_2$ or μM concentrations of Co(NH$_3$)$_6^{3+}$. Yeast whole cell extract, nuclear extracts, and phosphocellulose column fractions of yeast nuclear extracts were assayed by a gel retardation assay using either of these $^{32}$P-labelled DNA fragments as a probe. The gel retardation assay was carried out with the probe in the presence of 10 mM MgCl$_2$ and a 400-fold excess of sheared salmon sperm B-DNA. Under these conditions, the polymer assumes the Z-DNA conformation. A Z-DNA-specific antibody was used for positive control. 1 μl of each fraction of yeast nuclear extract obtained by salt elution from the phosphocellulose column with 0.2–0.5M potassium phosphate (pH 7.4) was added to the assays.

A distinctive band shift was detected in assays of the phosphocellulose column fractions of yeast nuclear extracts. Both whole cell extracts and nuclear extracts produced a similar band shift. The nuclear extract fractions that did not bind to B-form DNA (Winter and Varshavsky, 1989) showed significant gel retardation using the probe [$^{32}$P]poly(dG-m$^5$dC) in the Z-DNA form even in the presence of a 400-fold molar excess of sheared salmon sperm DNA. A similar band shift resulted from binding with polyclonal anti-Z-DNA antibody. The pooled fractions (FI) also showed binding activity to the oligonucleotide probe, [$^{32}$P](dG-Br$^5$dC)$_{22}$.

In order to determine if these band shifts were the result of authentic Z-DNA binding, negatively supercoiled plasmids of pUC19 and pUC19(GC) were used as competitor DNAs in gel retardation competition assays. In these assays, [$^{32}$P](dG-Br$^5$dC)$_{22}$ was incubated in the presence of a 2000-fold excess of sheared salmon sperm DNA with additions as follows: 1) no addition; 2) a monoclonal anti-Z-DNA antibody (mAb); 3) mAb plus additional 50 ng of negatively supercoiled plasmid pUC19 (without a Z-DNA insert); 4)

mAb plus 25 ng of negatively supercoiled pUC19(CG) (containing a Z-DNA segment); 5) fraction F1 yeast protein; 6) F1 plus additional 50 ng pUC19; and 7) F1 plus pUC19 (GC). pUC19(GC) contains a 14 bp (dG-dC)$_7$ insert that can adopt the Z-conformation upon negative supercoiling. pUC19(GC) was assayed for its resistance to BssHII digestion (Vardimon and Rich, 1983; Azorin et al., 1984) to confirm the presence of the Z-DNA prior to the assay.

The results showed that monoclonal anti-Z-DNA antibody (Moller et al., 1982), used as a positive control, exhibited specific complex formation in the presence of the competing plasmid pUC19, but not in the presence of supercoiled plasmid pUC19(GC), which contains Z-DNA. Similar binding specificity was observed when a partially purified yeast fraction (FI) was used instead of the anti-Z-DNA antibody. However, the complex observed with the protein fraction was more heterogeneous than that seen with the antibody. The Z-DNA binding activity of fraction FI was further purified using affinity chromatography to a poly(dG-m$^5$dC)-agarose column (FII) followed by Superose 12 (FIII) and Mono-S chromatography. The resultant active fraction (FIV) included a prominent 51 kDa protein that was still quite complex.

Identification of Zuotin by Southwestern Blotting

In order to identify the specific protein that interacts with the Z-DNA probe, a Southwestern blot was employed. Proteins in the Mono-S column fractions were transferred from a SDS-polyacrylamide gel to an Immobulon P membrane and exposed to conditions that favor renaturation. Subsequently, the filter was incubated in the presence of [$^{32}$P]poly(dG-m$^5$dC), stabilized in the Z-form by 15 mM MgCl$_2$ and a 300-fold excess of B-DNA (sheared salmon sperm DNA). An autoradiogram was made of the Southwestern blot and compared with a silver-stained gel of the Mono-S fractions.

The results showed that the poly(dG-m$^5$dC) probe bound a single polypeptide of ~51 kDa present in fractions 12 and 13, both of which were active in the band shift assay. There was also a weak signal in fraction 14. Although the fractions were quite complex, only the 51 kDa protein was detected by autoradiography. The putative Z-DNA binding protein was named zuotin (from the Chinese, zuo, meaning left).

Purification of Zuotin and Cloning of ZUO1

Approximately 5 μg of zuotin were gel-purified for amino acid composition analysis and N-terminal sequencing. The composition of hydrolyzed zuotin was obtained from the purified yeast protein and from the E. coli expressed or recombinant zuotin. Both were gel-purified and subjected to HCl hydrolysis, then, analyzed by HPLC with internal controls. The deduced composition of zuotin is derived from the DNA sequence of the open reading frame (ORF) of ZUO1. The amino acid composition of zuotin was 20.5% (Arg, Lys, and His), 18.5% (Glu and Asp), 14.1% (Thr, Ser, and Tyr) and 68.16% (Arg, Lys, Asp, Glu, Ser, Thr, Ala, and Leu). The amino acid composition of zuotin is shown in Table 4.

N-terminal sequencing yielded the following: MFSLPTLTSDI(E/D)V[EV](N)(H/S)(D), where [ ] and ( ) indicate moderate and low confidence assignments, respectively.

Degenerate 32mer oligonucleotides were designed by "reverse translation" of the N-terminal sequence. Alternative nucleotides were introduced at five positions in the oligonucleotide sequence. Nucleotides later determined to be mismatched are underlined. The oligonucleotides were used as a probe in Southern hybridization analysis of yeast genomic DNA. The Southern blot revealed a single hybridizing 2.4 Kb HindIII fragment. A yeast genomic EMBL3A library was subsequently screened and 14 clones isolated. Restriction mapping and Southern hybridization using the 32mer oligonucleotides revealed that one of the isolates contained a 2.4 Kb HindIII hybridizing fragment. This HindIII fragment was subcloned and the nucleotide sequence determined. The DNA sequence revealed an open reading frame (ORF), whose translated N-terminal sequence corresponded exactly to that of the N-terminal sequence determined from purified zuotin. To obtain the entire coding sequence of the ORF, a 3.1 Kb BamHI-EcoRI fragment was subcloned into the pBluescript vector (Stratagene), and the nucleotide sequence (SEQ ID NO:1) was determined by the dideoxy chain termination method. This sequence data is available from the EMBL sequence data bank under accession number X63612.

ZUO1 Encodes a 433 Residue Protein

The 3.1 Kb BamHI-EcoRI fragment contains the entire zuotin coding region (1291–2590), as well as 5' and 3' non-transcribed regions (SEQ ID NO:1). In FIG. 12, tracts of alternating (AT)$_n$, A or T in the 5' nontranscribed region that could serve as regulatory sites are underlined with single lines and labelled. A homopurine/pyrimidine tract (with one exception) in the coding region that can adopt an alternative DNA conformation is underlined with double lines. The potential polyadenylation site at the 3' end of the gene is indicated. There is a long ORF encoding a 433 amino acid (aa) protein with a calculated molecular weight of 49 kDa. A second ORF in the same orientation within ZUO1 potentially encodes a 168 amino acid polypeptide. It remains to be seen if there is a translated product from this second reading frame. The 5' region of the 3.1 Kb fragment also has another ORF containing 210 codons, which encodes a yeast analogue of the E. coli biotin synthetase gene (bioB).

The 5' non-transcribed region of ZUO1 contains three A/T-rich segments and two alternating AT segments that may act as regulatory domains from transcription of the gene. There is also a purine-rich tract in the coding region that could adopt a DNA conformation different from conventional B-DNA (McCarthy and Heywood, 1987). The coding region comprises 1299 base pairs and the transcript of ZUO1 is ~1.7 Kb. ZUO1 is localized on yeast chromosome VII near ADE3.

Zuotin has several interesting features: it consists of 13% alanine, 20.6% positively charged residues (lysine, arginine and histidine) and 18.5% negatively charged residues (aspartic acid and glutamic acid) (Table 4). It has a pI of 8.8. The charged residues are clustered at the C-terminal end and there is one segment with 12 charged residues in a row (FIG. 1; + and − indicate positively and negatively charged amino acids, respectively). There are two continuous perfect and one imperfect octad tandem repeats of alternating alanine and charged amino acids (lysine and glutamic acid) in the alanine/lysine and arginine rich region (heavy underlining).

Zuotin also contains several potential phosphorylation sites, including sequences recognized by protein kinase C (●), casein kinase II (O), cAMP-dependent protein kinase (▼), and tyrosine kinase (★), as predicted by Prosite (FIG. 1) (Bairoch, 1991). There are also two potential CDC28 (or cdc2) phosphorylation sites (KTPFVRR from 21–27 and KTPIP from 201–205 SEQ ID NO:2 (✱)) (Moreno and Nurse, 1990). It has a bipartite nuclear targeting sequence: KKKAKEAAKAAKKKNKR from 340–356 SEQ ID NO:2 wavy underlining; Robbins et al., 1991).

There are several regions that are predicted to form an α-helix (Chou and Fasman, 1978) and this includes the repeated octad segment (heavy underlining, FIG. 1). However, when a 16 residue peptide (EAK16) of the repeated segment was synthesized and examined by circular dichroism, a distinctive β-sheet structure was observed.

The zuotin protein is structurally similar to several known proteins. It shares a region of sequence similarity (residues 111–165) with DnaJ protein (SEQ ID NO:8), which is involved in DNA replication of bacteriophages λ and P1 (Liberek et al., 1988) and with several other yeast proteins: YDJ1 (SEQ ID NO:12); Caplan and Douglas, 1991), SIS1 (SEQ ID NO:11); Luke et al., 1991), SCJ1 (SEQ ID NO:9); Blumberg and Silver, 1991) and SEC63 (or NPL1) (SEQ ID NO:14); Sadler et al., 1989) (FIG. 13A). All of these proteins include the hexapeptide motif, KYHPDK (highlighted in bold, FIG. 13A). This hexapeptide motif is also present in both the small t and large T antigens of avian budgerigar fledgling disease virus (SEQ ID NO:13); Rott et al., 1988) and in the csp29 and csp32 proteins expressed in the retina and brain of Drosophila (SEQ ID NO:10); Zinsmaier et al., 1990). The consensus sequence shown in FIG. 13A SEQ ID NO:28 was obtained by computer analysis using the GeneWorks version 2.0 (1991) program. This consensus means that at least five identical amino acids are aligned in a row. − indicates negatively charged amino acids; Φ, nonpolar amino acids; and ., nonconserved amino acids.

There is also sequence similarity between another region of zuotin (residues 300–363) and several histone H1 variants, including human H1a, H1b and H1c, chicken H1.11L and H1.11R (SEQ ID NO:17), and sea urchin H1β and H1δ (SEQ ID NO:16). The conserved region is in the extended C-terminal tail of histone H1, a region rich in alanine, lysine and arginine residues. For example, the sequences from 300–363 in zuotin and 146–205 in sea urchin histone H1 (SEQ ID NO:16) are 64% similar and 46% identical.

The DnaJ similar region is located from amino acids 111 to 165 and the histone H1 similar region is located from amino acids 300 to 363 of zuotin.

Construction and Analysis of zuo1 Mutants

In order to generate an interrupted zuo1 allele, the 1.2 Kb HindIII fragment containing the S. cerevisiae URA3 gene was inserted at a unique HindIII site of the ZUO1 coding region. Wild type DNA has a 3.1 Kb EcoRI-BamHI fragment, whereas, the disrupted mutant has a 4.3 Kb fragment. The plasmid pZUO1::URA3 was then linearized and used to transform DM27, a diploid ura3 yeast strain. Diploid Ura+ transformants, expected to be heterozygous at the ZUO1 locus, were selected and confirmed to harbor disruption at the ZUO1 locus. The heterozygous diploid strains were subsequently sporulated and subjected to tetrad analysis. Tetrads yielded four viable colonies: two large and two small colonies, in which Ura+ phenotypes co-segregated with the small colonies (i.e., a slow growth phenotype). Southern blot analysis using DNA from four tetrads revealed that all clones with the slow growth phenotype harbor the 1.2 Kb insertion. The results showed that the insertion of URA3 at the ZUO1 locus produces a similar slow growth phenotype.

Expression of ZUO1 in E. coli

In order to verify that the cloned S. cerevisiae ZUO1 gene encodes the putative Z-DNA binding protein, ZUO1 was expressed in E. coli using a T7 expression system (Studier et al., 1990). ZUO1 was cloned in pET8c at the unique NcoI and BamHI sites. When the lacUV5 promoter was induced with IPTG, a protein band with an apparent molecular weight of ~51 kDa was detected. This protein was not seen in the cell extract from pET8C transformants induced with IPTG nor in the cell extract from uninduced pETZUO transformants. Analysis of the protein composition and the N-terminal sequence of the purified and the E. coli expressed or recombinant zuotin are essentially the same, indicating that zuotin was expressed correctly.

In attempting to purify zuotin expressed in E. coli, Applicants found that the recombinant zuotin was sequestered in inclusion bodies. However, enough material was in solution so that crude cell extracts and partially purified zuotin could be prepared and assayed by the band shift assay. Recombinant zuotin was partially purified by chromatography of crude cell extract from induced pETZU01 transformants through phosphocellulose. $^{32}$P-labelled poly(dG-m5dC) in the Z-form was incubated with the crude cell extract or with partially purified zuotin in the presence of sheared salmon sperm DNA, poly(dG-dC), or poly(dG-Br$^5$dC). Assays were run on: 1) labelled probe alone; 2) crude cell extract from induced pET8c transformants; 3) crude cell extract from uninduced pETZU01 transformants; 4) crude cell extract from induced pETZU01 transformants; 5) partially purified recombinant zuotin; 6) partially purified yeast zuotin; 7)–10) partially purified recombinant zuotin with 20-, 40-, 100-, and 200-fold excess of salmon sperm DNA; 11)–12) partially purified recombinant zuotin with 20- and 40-fold excess of poly(dG-dC); 13)–14) partially purified recombinant zuotin with 20- and 40-fold excess of poly(dG-Br$^5$dC); 15)–17) partially purified yeast zuotin with 20-, 40-, and 200-fold excess of salmon sperm DNA; 18) partially purified yeast zuotin with 40-fold excess of poly(dG-dC); 19) partially purified yeast zuotin with 40-fold excess of poly (dG-Br$^5$dC); and 20) an anti-Z-antibody (as control).

These gel shift assays showed that partial purification through phosphocellulose yielded a fraction with Z-DNA binding ability. The strongly shifted band bound to labelled poly(dG-m$^5$dC) even in the presence of a 40-fold excess of salmon sperm DNA. On adding a 40-fold excess of poly (dG-dC), which can form Z-DNA under certain conditions, a somewhat weaker band was visible. Similar results were found with zuotin isolated from yeast. It is interesting that the band shift with yeast zuotin migrated slightly further towards the positive side of the gel than the bacterially expressed zuotin. It is possible that this difference could be due to differences in phosphorylation or other post-translational modifications that were not carried out in E. coli. Furthermore, the yeast zuotin bound Z-DNA more tightly than the bacterially expressed zuotin. It is known, for example, that phosphorylation modifies the DNA binding activity of the yeast centromere binding protein CBF3 (Lechner and Carbon, 1991). Analysis of the Zuotin sequence using the Prosite computer program (Bairoch, 1991) suggests that zuotin may be phosphorylated. Attempts are now being made to express zuotin in other systems, including those which phosphorylate proteins.

DNA Binding Properties of Zuotin

Yeast protein fractions containing zuotin are able to bind both poly(dG-m$^5$dC) and oligo(dG-BR$^5$dC)$_{22}$ in the Z-form as well as negatively supercoiled pUC19(GC) containing a Z-form segment in the presence of competitor B-DNA. Since zuotin has not been purified to homogeneity, it is difficult to obtain a precise Z-DNA binding constant. The yeast zuotin is estimated to have a several hundred-fold enhanced affinity for Z-DNA relative to B-DNA under the experimental conditions used, while the E. coli expressed zuotin binds less tightly. It would not be surprising if proteins which interact with Z-DNA have binding motifs different from the binding motifs of several proteins known to interact with B-DNA. B-DNA has distinct major and minor grooves, and B-DNA binding proteins tend to either anchor their binding motifs in the major grooves or lie along the minor grooves (reviewed in Seeman et al., 1976; Pabo and Sauer, 1984; Churchill and Travers, 1991). Such binding to B-DNA is relatively tight and, in some cases, very specific. On the other hand, Z-DNA does not have a distinct major groove nor a highly accessible minor groove. Thus, it is possible that a Z-DNA binding protein would not be able to anchor its binding motif to the region corresponding to the major groove. It is possible that the binding constants of Z-DNA binding proteins are lower than those of B-DNA proteins. It has been shown that many DNA sequences can adopt the left-handed Z-conformation (Rich et al., 1984). Thus, proteins that recognize Z-DNA may be conformationally specific as well as sequence specific.

The binding of both yeast zuotin and bacterially expressed zuotin to poly(dG-m$^5$dC) cannot be competed by 40-fold excess of poly(dG-dC), 200-fold excess of poly(dA-dT), nor several thousand-fold of salmon sperm DNA. However, a mere 4-fold excess of poly(dG-Br$^5$dC) in the Z-form completely inhibits zuotin binding to the probe. These results suggest that zuotin may recognize the conformation of DNA rather than specific sequences per se. Another example of a protein that recognizes DNA conformation specifically is HMG1 (high mobility group protein). HMG1 and proteins containing HMG1 domains bind DNA not by its sequence but rather by the DNA conformation at the crossing of two duplexes (Bianchi et al., 1992; Lilley, 1992).

The Biological Function of Zuotin

Previous studies have suggested that potential Z-forming sequences, i.e., (GC/GC)n, (GT/AC)n and other alternating purine/pyrimidine segments, exist in the intergenic regions of many organisms, including those of yeast (Hamada et al., 1982). The GT/AC segments have been implicated in inducing homologous DNA recombination in vivo (Bullock et al., 1986; Treco and Arnheim, 1986; Wahls et al., 1990). Also, a DNA strand transferase from human cells has been partially purified using a Z-DNA affinity column (Fishel et al., 1988). Recently, it has been shown that specific alternating purine/pyrimidine segments in the upstream region of c-myc form Z-DNA during active transcription.

The precise biological function of zuotin is not known at the present time. Since zuotin appears to be of nuclear origin, binds to DNA, is relatively abundant and may potentially be phosphorylated by protein kinases and dephosphorylated by phosphatases during the cell cycle, it could be involved in chromosome organization. The threonine within the KTPFVRR and KTPIP sequences may be phosphorylated by the S. cerevisiae CDC28-CLN complex during the cell cycle.

Computer sequence comparison analysis revealed that two different regions of zuotin have similarities with known proteins. The first region of zuotin (residues 111–165) has 46% identity and an overall 70% similarity with the N-terminus of E. coli DnaJ protein (residues 16–67) (SEQ ID NO:8). The DnaJ protein is a heat shock protein involved in protein folding; it is also active in phage λ and P1 replication in vivo and in vitro through its interaction with DnaB helicase (Liberek et al., 1988; Zylicz et al., 1989). This region of zuotin also shares similarity with several other yeast proteins: YDJ1 (a yeast DnaJ homolog), which may be involved in protein assembly into the endoplasmic reticulum and nucleus (SEQ ID NO:12); Caplan and Douglas, 1991); SCJ1, which is involved in protein sorting (SEQ ID NO:9); Blumberg and Silver, 1991); and SIS1, which is an essential protein and may be involved in yeast DNA replication by mediating a specific protein-protein interaction (SEQ ID NO:11); Luke et al., 1991). Similarity was also found to the yeast protein SEC63 (or NLS1), which is important for protein assembly into the endoplasmic reticulum and the nucleus (SEQ ID NO:14); Sadler et al., 1989). Both YDJ1 and SIS1 have several cysteines that could potentially form a zinc finger DNA binding motif, but zuotin has only one cysteine and no zinc finger motif could be found. All the above proteins have a conserved hexapeptide, KYHPDK, except SEC63, in which F has replaced Y. This peptide motif may play an essential role in these diverse proteins. Moreover, both small t and large T antigens (SEQ ID NO:13) of the arian polyomavirus, budgerigar fledgling disease virus, as well as the csp29 and csp32 (SEQ ID NO:10) proteins expressed in Drosophila retina and brain have this identical hexapeptide motif (Zinsmaier et al., 1990). Recently, a human nuclear protein HDJ-1 has also been shown to be similar at both the N- and C-termini to the DnaJ protein (SEQ ID NO:15); Raabe and Manley, 1991).

A second region of similarity in zuotin (residues 300–363) is related to histone H1 and some of its variants, such as human H1a, H1b and H1c, chicken H1.11L and H1.11R (SEQ ID NO:17), and sea urchin H1β and H1δ (SEQ ID NO:16) (FIG. 13B). It is significant that histones H2A, H2B, H3 and H4 do not have regions similar to zuotin. Calf thymus histone H1 has been shown to have a higher affinity to Z-DNA than to B-DNA and it is able to convert Z-DNA to B-DNA, a transition that can be measured using circular dichroism spectroscopy (Russell et al., 1983; Mura and Stollar, 1984). Also, the Drosophila histone H1 has been previously purified using a Z-DNA affinity column and Z-DNA binding assays. It is possible that zuotin has some elements of histone H1-related activity in yeast.

A subportion of this histone-like region from amino acids 306 to 339 (heavily underlined in FIG. 1) is a likely candidate for a DNA-binding domain. In related studies, Applicants found that the peptides KAKAK and KAK were able to bind to B-DNA and convert it to the Z conformation. Amino acid substitutions at the middle lysine of KAKAK resulted in a loss of activity, but changes at the carboxyl-terminal K did not significantly affect activity. A peptide, KAHAK SEQ ID NO:30, was active in converting B-DNA to Z-DNA only when the histidine was protonated (at low pH). The KAKAX motif SEQ ID NO:31 (where X is variable) occurs twice in the 306–339 region and also occurs in the peptide, EAK16. These observations are consistent with the structural similarity of this region to histone H1.

In an attempt to see whether zuotin is found in other organisms, a Southern "zooblot" was carried out in which various DNAs were probed with zuotin DNA. Of 12 plant and animal species that were probed under low stringency, all were negative except yeast. This suggests that zuotin is a yeast-specific protein.

Mutant yeast cells in which ZUO1 was disrupted exhibit a slow growth phenotype. Thus, the function of ZUO1 appears not to be essential, rather it may be involved in some activity that is needed to maintain rapid cell growth.

MATERIALS AND METHODS

Yeast Strains and Media

The genotype and sources of yeast S. cerevisiae used in this work are as follows: DB2670, MATα, his3-Δ200, ura3-52, can 1, pep4::HIS3, prb1-Δ1.6R was obtained from D. Botstein; 20B-12, MATα, pep4-3, trp1 has been previously described (Jones, 1977); DM27, MATα/α, his3/HIS3, leu2/LEU2, ade2/ADE2 ura3/ura3, trp1/trp1, cyh/CYH was obtained from D. Dawson. Cells were grown in YPD medium (1% yeast extract, 2% bactopeptone and 2% glucose). SD medium contained 0.6% Difco yeast nitrogen base without amino acids and 2% glucose. Nutrients essential for auxotropic strains were supplied at concentrations recommended by Sherman et al. (1986). The plasmid, pUC19(GC), was obtained from B. Johnston. Characterization of the anti-Z-DNA Z-22 monoclonal antibody and polyclonal goat anti-Z-DNA antibody have been described (Moller et al., 1982).

Preparation of the Poly (dG-m$^5$dC) Affinity Matrix

Poly(dG-m$^5$dC) DNA (Pharmacia) (1.6 mg in 3 ml) was digested to an average size of ~600 bp using DNase I in 50 mM Tris-HCl (pH 7.5), 30 μg/ml BSA in the presence of 2 mM MnCl$_2$ to produce blunt ends (Maniatis et al., 1982). The digested DNA was deproteinized and resuspended in T4 DNA polymerase buffer in the absence of dNTP and incubated with T4 DNA polymerase at 10° C. for 10 minutes. Subsequently dGTP and biotinylated dCTP (ENZO) were added to 1 mM final concentration, and incubation was continued at 37° C. for 2 hours. DNA was then separated from unincorporated nucleotides by phenol and chloroform extraction, followed by two ethanol precipitations. Then, DNA was dissolved in 0.1M NaCl, 1 mM EDTA, 10 mM Tris-HCl (pH 7.5) and incubated with 1 ml of streptavidin-agarose (BRL) overnight by gentle inversion. Under these conditions, more than 60% of the input DNA was bound to streptavidin-agarose as determined by $A_{260}$ measurement after pelleting the agarose. The DNA matrix was then washed extensively with 40 column volumes of buffer (10 mM Tris-HCl, pH.7.5, 50 mM KCl and 15 mM MgCl$_2$). The column wash was assayed for unbound DNA (using the BluGene non-radioactive nucleic acid detection system, BRL) to assess the column stability.

Purification and Sequencing of Zuotin

The preparation of crude nuclear fractions has been described previously (Winter and Varshavsky, 1989). Crude total cell extract (from strain DB2670) was prepared from mid-log phase yeast cells (18 L at ~2.4×10$^7$ cells/ml). Yeast cells were collected at 4500× g for 10 minutes at 4° C. and washed twice with water. The cell pellet was resuspended in 600 ml of 0.2M potassium phosphate (pH 7.5), 5 mM EDTA, 1 mM phenylmethylsulfonyl fluoride (PMSF), 0.8 μg/ml pepstatin A and 10% glycerol. The final volume was ~800 ml. The cell suspension was processed through a high pressure compressor at 900 psi ~50 passages to break the cells. The suspension was then centrifuged at 12,000× g for 10 minutes at 4° C. The supernatant (~720 ml) was frozen at −80° C. Fractionation of whole cell extract on a phosphocellulose P-II column and on a Mono-S column were as described by Winter and Varshavsky (1989). The pooled fraction (FI) containing binding activity to poly(dG-m$^5$dC) in the presence of sheared salmon sperm DNA was diluted 6-fold to achieve a potassium phosphate concentration of ~50 mM (420 ml). MgCl$_2$ was then added to a final concentration of 15 mM for loading on the poly(dG-m$^5$dC) affinity column. The column was washed with 10 volumes of the column buffer and eluted with a linear gradient of 25 ml 0.1–1.0M KCl without MgCl$_2$ (FII).

The eluted proteins were then loaded on a Superose-12 gel filtration column. One ml fractions were collected and asseyed for the Z-DNA binding activity (FIII). These fractions were pooled, diluted 3-fold and loaded on a Mono-S column. The Mono-S column was washed extensively and eluted with a linear gradient 47 ml of buffer, 0–1.0M NaCl, in 10 mM sodium phosphate (pH 7.2). The 1 ml fractions containing Z-DNA binding activity (FIV) were analysed by SDS-PAGE.

For protein composition and sequence analysis, the pooled Mono-S column fractions 12 and 13 were resolved on a 9% polyacrylamide-SDS gel. After electrophoresis, the protein was electroblotted on Immobulon (Millipore), briefly stained with Coomassie Blue and washed. The band with an apparent molecular weight of 50 kDA was excised and ¼ of the sample was used for amino acid composition analysis. The remaining sample was N-terminal sequenced by automated Edman degradation in an Applied Biosystems 470A Protein Sequencer equipped with on-line 120A PTH analyser.

Band Shift and Competition Experiments

A gel retardation assay was employed to detect proteins with affinity to left-handed Z-DNA. In these assays, two kinds of left-handed DNA probes were used. One was poly(dG-m$^5$dC) (Pharmacia) stabilized in the left-handed Z-form by 15 mM MgCl$_2$. The DNA probe was made as follows: DNA polymer was digested with DNase I in the presence of 2 mM MnCl$_2$ and fragment of ~600–1000 bp were gel purified and labelled with T4 DNA polymerase in the presence of dCTP and [α-$^{32}$P]dGTP (3000 Ci/mM) (Maniatis et al., 1982). The other probe was derived from a synthetic 44mer oligo(dG-Br$^5$dC)$_{22}$, labelled using Klenow polymerase with [α-$^{32}$P]dGTP, and stabilized in the Z-DNA conformation by 10 mM MgCl$_2$, or 0.1 mM Co(NH$_3$)$_6^{3+}$. In the assay reaction, 2 μl of diluted fraction samples were incubated for 20 minutes at room temperature in 20 μl of 50 mM Tris-HCl (pH 8.0), 15 mM MgCl$_2$, 5% sucrose, 0.1% Triton X-100, 10 mM β-mercaptoethanol, a 2000-fold excess of sheared salmon sperm DNA, and the labelled Z-DNA probe. In the competition assays, supercoiled pUC19 and pUC19(CG) were added to the reaction samples separately. The samples were then electrophoresed in 1.5% agarose for poly(dG-m$^5$dC) (10 mM MgCl$_2$, 1X TBE, pH 8.4) or 4% polyacrylamide for (dG-Br$^5$dC)$_{22}$ (1X TBE, pH 8.4). After electrophoresis, the gel was dried and exposed to X-ray film.

Southwestern Blotting

Mono-S column fractions containing proteins were electrophoresed on 9% polyacrylamide-SDS gel, as described by Laemmli (1970). After electrophoresis, the gel was soaked in the running buffer without SDS but with 20% methanol at room temperature for 45 minutes with agitation. The proteins were then blotted onto two sheets of Immobulon P membrane (Millipore) at 1.5 mA/cm$^2$ at room temperature for 60 minutes. After transfer, the membrane was washed once with 5% milk powder, 30 mM HEPES (pH 7.4) (Celenza and Carlson, 1986); then, washed three times (3 minutes each) with 10 mM Tris-HCl, 50 mM NaCl, 1 mM EDTA, 10 mM MgCl$_2$ (STEM). After washing, the membrane was incubated with 15 ml of the above buffer containing 10 μg/ml sheared salmon sperm DNA. A DNA probe (average size 1300 bp) (at 2.55×10$^6$ c.p.m./ml of poly(dG-m$^5$dC)) was added to a final concentration of 30 ng/ml and the incubation continued for 1 hour at room temperature with gentle agitation (50 r.p.m.). In this buffer with 10 mM MgCl$_2$ the polymer is in Z-DNA conformation (Behe and Felsenfield, 1981). The membrane was then washed four times (8 minutes each) with STEM at room temperature. The membrane was air-dried and exposed to X-ray film.

Cloning and Sequencing of ZUO1

The first 11 amino acids of the N-terminal sequence of zuotin (MFSLPTLTDI) were used to design oligonucleotides, with yeast codon usage as a guideline (Sharp et al., 1986). The pools contained an equal molar mixture of 64 different 32mer sequences as follows:

(SEQ ID NO: 22)
5'-ATGTTTCTTTGCCAACTTTGACTTCTGATAT-3'.
      C     T C        C        C

These oligonucleotides were gel-purified and labelled using [γ-$^{32}$P]ATP and T4 polynucleotide kinase to a specific activity 200–500 μCi/μg. The labelled oligonucleotides were first used in genomic Southern blot hybridization to determine optimal conditions for screening a phage λ library of yeast DNA. For this, yeast DNA was digested with HindIII, separated on an 1% agarose gel and blotted onto a Gene Screen filter (New England Nuclear). The filter was hybridized at 40° C. in 4.5% SDS, 0.34M NaCl, 1 mM Na-EDTA, 10 mg/ml BSA and 0.16M sodium phosphate buffer (pH 7.0) overnight. The filters were then washed at temperatures between 40 and 80° C. with washing steps at 5° C. in 3M tetramethyl-ammonium chloride, 2 mM EDTA, 0.1% SDS, and 50 mM Tris-HCl (pH 8.0), as described by Wood et al. (1985). At the washing temperature of 65° C., there was a single hybridization band of ~2.4 Kb. This temperature was chosen for screening a *S. cerevisiae* genomic phage γ EMBL3A DNA library. Screening of the phage EMBL3A library was essentially the same as described by Winter and Varshavsky (1989). Thirteen positive phage plaques were isolated. Phage DNAs from 11 clones were purified from the confluent plate lysates. The DNA was then digested with several restriction enzymes and a Southern blot was performed, as described previously. The restriction pattern and hybridization analysis revealed that the clones fell into three classes. One phage clone with a 3.1 Kb EcoRI and BamHI fragment was chosen for subcloning into pBluescript. Sequence analysis was carried out as described by Sanger et al. (1977). The 3.1 Kb DNA fragment was sequenced on both strands with synthetic oligonucleotides as primers using the USB Sequenase kit (Version 2.0).

Expression of Zuotin in *E. coli*

Zuotin was expressed in *E. coli* using the T7 pET expression system (Studier et al., 1990). In order to insert ZUO1 into the NcoI site of the pET8c vector, two bases flanking the initiation ATG were modified: at −1 (GC) and at +4 (TG). This produced an amino acid change immediately after Met of (Phe→Val). An oligonucleotide of 25 bases, CAAGAGTAACCATGGTTTCTTTACC (SEQ ID NO:18), was synthesized and used as a primer for PCR amplification. A fragment of 1.8 Kb containing the entire coding region of zuotin was amplified by polymerase chain reaction (PCR) from pSKIIZUO1 and ligated into pET8c which was previously digested with NcoI and BamHI and dephosphorylated.

The pETZUO1 clones were isolated by colony hybridization using the coding region of ZUO1 as a probe. Extensive restriction mapping and sequencing using the T7 primer and several internal primers confirmed the correct in-frame cloning of ZUO1. Furthermore, the zuotin expressed in *E. coli* had its N-terminal region sequenced and its composition analysed by hydrolysis in order to confirm expression of the correct protein (Table 4.

*E. coli* strain, BL21E3LysS, which carries T7 RNA polymerase in the chromosome of the host under the control of the lacUV5 promoter, was transformed with pETZUO1. The transformants were induced with 0.5 mM IPTG after the cells had reached a density of 0.5 O.D. ($A_{600}$). Cells were harvested 3 hours after induction, lysed, treated and analysed as described by Sambrook et al. (1989).

After cells were lysed by sonication, the cell suspension was centrifuged at 8000× g for 20 minutes at 4° C., and both supernatant and pellet were saved. The pellet was resuspended in buffer containing 10 mM Tris-HCl, 50 mM NaCl and 1 mM PMSF, and then urea was added to a final concentration of 4M in order to denature the inclusion bodies. The suspension was stirred at 4° C. for 4 hours. The suspension was then dialysed overnight at 4° C. with three changes of buffer. The dialysed suspension was centrifuged at 10,000× g for 30 minutes. The supernatant was then loaded on the phosphocellulose column. The column was washed in 100 mM $KH_2PO_4$ buffer and eluted with 1.0M $KH_2PO_4$. The eluent was dialyzed and used for characterization.

Construction of zuo1 Disruption Mutants

Figure 2:
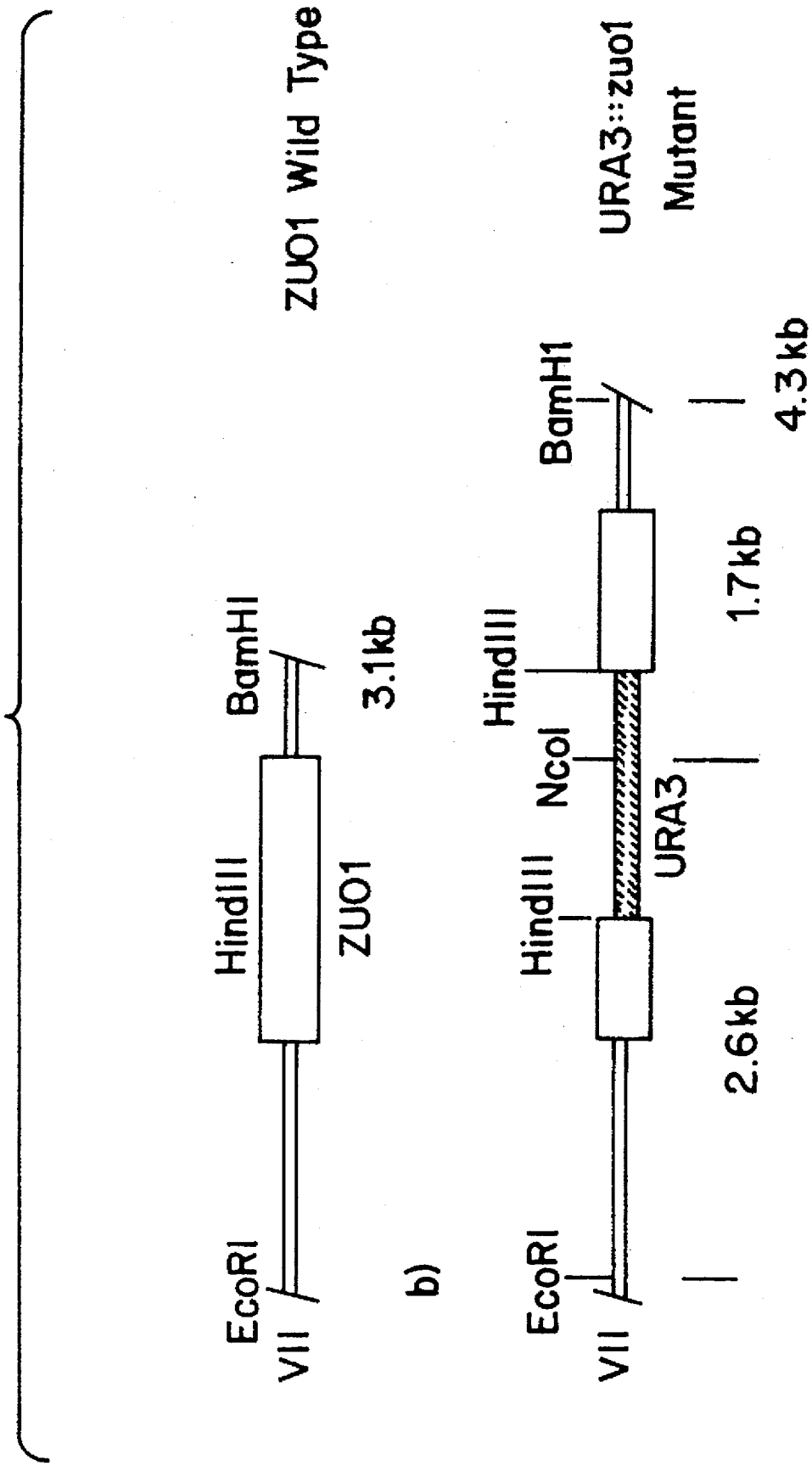
FIG. 2 is a restriction map of the wild type ZUO1 locus and the URA3::zuo1 disrupted locus.
Figure 3A:
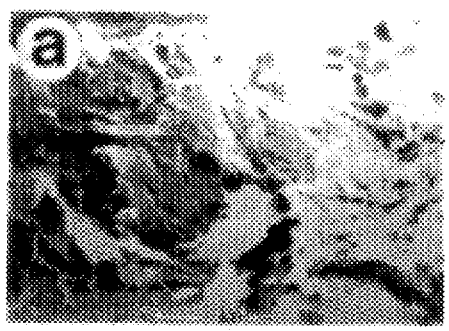
FIGS. 3A–3H are serial photographs of membranes under scanning electron microscopy (SEM).
Figure 3E:
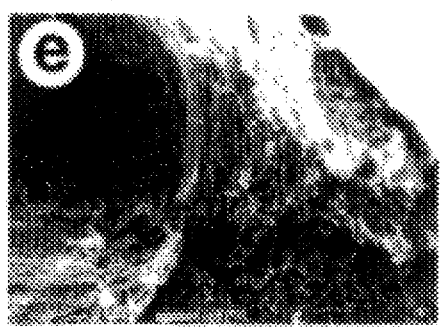
Figure 3B:
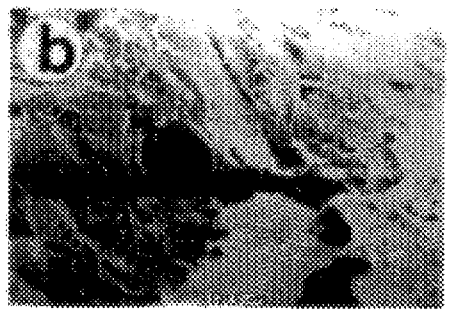
Figure 3F:
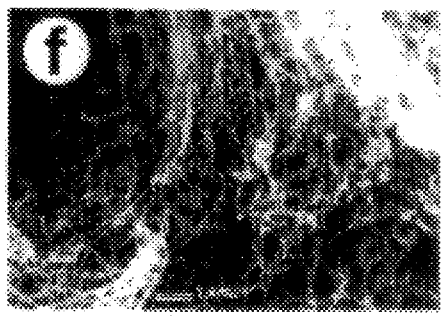
Figure 3C:
Figure 3G:
Figure 3D:
Figure 3H:
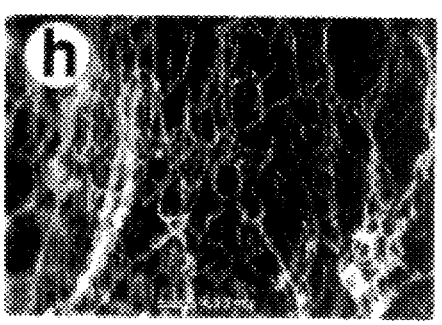

The gene disruption method of Rothstein (1983) was used for generating the zuo1 mutants in the yeast genome. A 1.17 Kb HindIII fragment containing URA3 was inserted at the unique HindIII site within the coding region of ZUO1 (corresponding to amino acid position 186). The DNA was then cut with EcoRI and BamHI, and the released fragment was used to transform a diploid *S. cerevisiae* DM27. Standard techniques were used for yeast transformation, sporulation and tetrad dissection (Sherman et al., 1986). Both orientations of the URA3 insert were used and yielded the same results (FIG. 2).

Computer Analysis of Zuotin

The predicted structure of zuotin was analysed by computer algorithms using Pepplot, FastA, BLAST and others, in the Genetics Computer Group (GCG) package, as installed at the Whitaker College Computer Facility at the Massachusetts Institute of Technology. GeneWorks Version 2.0 (1991, Intelligenetics, Inc., Mountain View) was used for zuotin alignment with DnaJ and other proteins.

TABLE 1

| Peptide | Sequence[a] | DMEM[b] | PBS | Water | Structure[c] |
|---|---|---|---|---|---|
| EAK16 | Ac—HN—AEAEAKAKAEAEAKAK—CONH$_2$ | ++++ | ++++ | − | β |
| EAK12 | Ac—HN—AEAKAEAEAKAK—CONH$_2$ | ++ | + | − | α, β |
| EAK8 | H$_2$N—AEAEAKAK—COOH | − | − | − | RC |
| ARD16 | H$_2$N—ARARADADARARADAD—COOH | ++++ | ++++ | − | ND |
| ARD8 | H$_2$N—ARARADAD—COOH | − | − | − | ND |
| β-Amyloid (1–28) | H$_2$N—DAEFRHDSGYEV— | | | | |

TABLE 1-continued

| Peptide | Sequence[a] | DMEM[b] | PBS | Water | Structure[c] |
|---|---|---|---|---|---|
| | HHQKLVFFAEDVGSNK—COOH | – | – | – | RC, α, β |
| β-Amyloid (25–35) | H₂N—GSNKGAIIGLM—CONH₂ | – | – | – | ND |
| Substance P | H₂N—RPKQQFGLM—COHN₂ | – | – | – | ND |
| Spantide | H₂N—(D)RPKPQQ(D)WL(D)L—CONH₂ | – | – | – | ND |

[a]One letter amino acid code is used.
(D) in Spantide is a D amino acid incorporated into the peptide.
[b]The + and – denotes the presence and absence of the membranous structure, respectively.
[c]α, α-helix.
β, β-sheet.
RC, random coil.
ND, not determined
(EAK16 is 310–325 of SEQ ID NO: 2.
EAK12 is SEQ ID NO: 24.
EAK8 is 310–317 of SEQ ID NO: 2.
ARD16 is SEQ ID No: 3.
ARD8 is 1–8 of SEQ ID NO: 3.
β-Amyloid (1–28) is SEQ ID NO: 4.
β-Amyloid (25–35) is SEQ ID NO: 5.
Substance P is SEQ ID NO: 6.
Spantide is SEQ ID NO: 7.)

TABLE 2

Potential membrane-forming peptides

| Name | Sequence (N → C) | |
|---|---|---|
| KAE16 | AKAKAEAEAKAKAEAE | (SEQ ID NO:32) |
| AKE16 | AKAEAKAEAKAEAKAE | (SEQ ID NO:33) |
| EKA16 | EAKAEAKAEAKAEAKA | (SEQ ID NO:34) |
| KEA16 | KAEAKAEAKAEAKAEA | (SEQ ID NO:35) |
| AEK16 | AEAKAEAKAEAKAEAK | (SEQ ID NO:36) |
| DAR16 | ADADARARADADARAR | (SEQ ID NO:37) |
| ARD16 | ARADARADARADARAD | (SEQ ID NO:38) |
| DRA16 | DARADARADARADARA | (SEQ ID NO:39) |
| RDA16 | RADARADARADARADA | (SEQ ID NO:40) |
| ADR16 | ADARADARADAPADAR | (SEQ ID NO:41) |
| ARDAKE16 | ARADAKAEARADAKAE | (SEQ ID NO:42) |
| AKEW16 | AKAEARADAKAEAPAD | (SEQ ID NO:43) |
| ARKADE16 | ARAKADAEARAKADAE | (SEQ ID NO:44) |
| AKRAED16 | AKARAEADAKARADAE | (SEQ ID NO:45) |
| AQ16 | AQAQAQAQAQAQAQAQ | (SEQ ID NO:46) |
| VQ16 | VQVQVQVQVQVQVQVQ | (SEQ ID NO:47) |
| YQ16 | YQYQYQYQYQYQYQYQ | (SEQ ID NO:48) |
| HQ16 | HQHQHQHQHQHQHQHQ | (SEQ ID NO:49) |
| AN16 | ANANANANANANANAN | (SEQ ID NO:50) |
| VN16 | VNVNVNVNVNVNVNVN | (SEQ ID NO:51) |
| YN16 | YNYNYNYNYNYNYNYN | (SEQ ID NO:52) |
| HN16 | HNHNHNHNHNHNHNHN | (SEQ ID NO:53) |
| ANQ16 | ANAQANAQANAQANAQ | (SEQ ID NO:54) |
| AQN16 | AQANAQANAQANAQAN | (SEQ ID NO:55) |
| VNQ16 | VNVQVNVQVNVQVNVQ | (SEQ ID NO:56) |
| VQK16 | VQVNVQVNVQVNVQVN | (SEQ ID NO:57) |
| YNQ16 | YNYQYNYQYNYQYNYQ | (SEQ ID NO:58) |
| YQN16 | YQYNYQYNYQYNYQYN | (SEQ ID NO:59) |
| HNQ16 | HNHQHNHQHNHQHNHQ | (SEQ ID NO:60) |
| HQN16 | HQHNHQHNHQHNHQHN | (SEQ ID NO:61) |
| AKQD18 | AKAQADAKAQADAKAQAD | (SEQ ID NO:19) |
| VKQ18 | VKVQVDVKVQVDVKVQVD | (SEQ ID NO:62) |
| VKQ18 | VKVQVDVKVQVDVKVQVD | (SEQ ID NO:63) |
| HKQ18 | HKHQHDHKHQHDHKHQHD | (SEQ ID NO:64) |

TABLE 3

Optical proportion of EAK16 at different temperature

| Temp (°C.) | λ₁ 218 nm | −[Θ₁] X1,000 | λ₂ 195 nm | [Θ₂] X1,000 | Ratio [Θ₂]/[Θ₁] |
|---|---|---|---|---|---|
| 25 | | 16 | | 62 | 3.9 |
| 37 | | 15 | | 60 | 4.0 |

TABLE 3-continued

Optical proportion of EAK16 at different temperature

| Temp (°C.) | λ₁ 218 nm | −[Θ₁] X1,000 | λ₂ 195 nm | [Θ₂] X1,000 | Ratio [Θ₂]/[Θ₁] |
|---|---|---|---|---|---|
| 55 | | 14 | | 55 | 3.9 |
| 70 | | 13 | | 54 | 4.1 |
| 90 | | 12.5 | | 50 | 4.0 |

TABLE 4

Amino acid composition analysis of zuotin

| | Hydrolysis | | Deduced from |
|---|---|---|---|
| | E. coli (%) | Yeast | DNA (%) |
| Arg | 5.7 | 7.6 | 6.0 |
| Lys | 9.2 | 11.9 | 12.9 |
| His | 3.1 | 1.4 | 1.6 |
| Glu | (11.5) | (12.1) | 9.7 |
| Gln | | | 2.3 |
| Asp | (11.0) | (11.5) | 8.8 |
| Asn | | | 3.2 |
| Ser | 7.0 | 7.4 | 6.9 |
| Thr | 4.4 | 5.0 | 5.1 |
| Tyr | 2.4 | 1.8 | 2.1 |
| Ala | 11.2 | 13.0 | 12.9 |
| Val | 6.3 | 4.8 | 5.5 |
| Leu | 6.8 | 6.6 | 5.8 |
| Ile | 3.6 | 3.0 | 3.2 |
| Phe | 3.8 | 4.5 | 5.1 |
| Trp | 0.0 | 0.0 | 1.4 |
| Pro | 4.0 | 3.2 | 3.5 |
| Gly | 5.0 | 6.1 | 3.0 |
| Met | 0.7 | 0.1 | 0.7 |
| Cys | 0.0 | 0.0 | 0.2 |

The numbers in parentheses are combined percentages of Glu/Gln and Asp/Asn as they are individually indistinguishable in the hydrolytic analysis.

References

Azorin et al., *Proc. Nat. Acad. Sci. USA* 81:5714–5718 (1984)

Bairoch, *Nucleic Acids Res.* 19 supp.:2241–2245 (1991)

Barrow and Zagorski, *Science* 253:179–182 (1991)

Behe and Felsenfeld, *Proc. Natl. Acad. Sci. USA* 78:1619–1623 (1981)

Bianchi et al., *EMBO J.* 11:1055–1063 (1992)

Blaho and Wells, *J. Biol. Chem.* 262:6082–6088 (1987)

Blumberg and Silver, *Nature* 349:627–629 (1991)

Brack and Orgel, *Nature* 256:383–387 (1975)

Bullock et al., *Mol. Cell. Biol.*, 6:3948–3953 (1986)

Caplan and Douglas, *J. Cell Biol.* 114:609–621 (1991)

Celenza and Carlson, *Science* 233:1175–1180 (1986)

Chou and Fasman, *Annu. Rev. Biochem.* 47:251–276 (1978)

Churchill and Travers, *Trends Biochem. Sci.* 183:92–97 (1991)

Erickson, *Scientific American*, Sep. 1992, pp. 163–164

Fishel et al., *Proc. Natl. Acad. Sci. USA* 85:36–40 (1988)

Gay et al., *FEBS Letters* 291:87–91 (1991)

Halverson et al., *Biochemistry* 29:2639–2644 (1990)

Hamada et al., *Proc. Natl. Acad. Sci. USA* 79:6465–6469 (1982)

Hilbich et al., *J. Mol. Biol.* 50:149–165 (1991)

Iqbal and Wisniewski, in: *Alzheimer's Disease: The Standard Reference*, Reisberg (ed.), Free Press, Collier Macmillan Publishers, London, 1983, pp. 48–56

Jaworski et al., *Science* 238:773–777 (1987)

Jones, *Genetics* 85:23–33 (1977)

Kirschner et al., *Proc. Natl. Acad. Sci. USA* 84:6953–6957 (1987)

Laemmli, *Nature* 227:680–682 (1970)

Lafer et al., *EMBO J.* 4:3655–3660 (1985)

Lechner and Carbon, *Cell* 64:717–725 (1991)

Liberek et al., *Proc. Natl. Acad. Sci. USA* 85:6632–6636 (1988)

Lilley, *Nature* 357:282–283 (1991)

Liu and Wang, *Proc. Natl. Acad. Sci. USA* 84:7024–7028 (1987)

Lizardi, *Cell* 18:581–589 (1979)

Luke et al., *J. Cell Biol.* 114:623–638 (1991)

Maniatis et al., *Molecular Cloning: A Laboratory Manual*, Cold Spring Harbor Laboratory Press, Cold Spring Harbor, N.Y., 1982

Marqusee and Baldwin, *Proc. Natl. Acad. Sci. USA* 84:8898–8902 (1987)

Marqusee et al., *Proc. Natl. Acad. Sci USA* 86:5286–5290 (1989)

McCarthy and Heywood, *Nucleic Acids Res.* 15:8069–8085 (1987)

Moller et al., *J. Biol. Chem.* 257:12081–12085 (1982)

Moreno and Nurse, *Cell* 61:549–551 (1990)

Mura and Stollar, *Biochemistry* 23:6147–6152 (1984)

Naylor and Clark, *Nucleic Acids Res.* 18:1595–1601 (1990)

Nordheim and Rich, *Nature* 303:674–679 (1983)

Osterman and Kaiser, *J. Cell. Biochem.* 29:57–72 (1985)

Pabo and Sauer, *Annu. Rev. Biochem.* 53:293–322 (1984)

Padmanabhan et al., *Nature* 344:268–270 (1991)

Pauling, *Nature of the Chemical Bond and the Structure of Molecules and Crystals: An Introduction to Model Structural Chemistry*, 3rd ed., Cornell University Press, Ithaca, New York, 1960

Pears, *Histochemistry, Theoretical and Applied*, 2nd Ed., Little, Brown and Company, Boston, 1960

Peck et al., *Proc. Natl. Acad. Sci. USA* 79:4560–4564 (1982)

Piggion et al., *Biopolymers* 11:633–643 (1972)

Raabe and Manley, *Nucleic Acids Res.* 19:6645 (1991)

Rahmouni and Wells, *Science* 246:358–363 (1989)

Rich et al., *Annu. Rev. Biochem.* 53:791–864 (1984)

Rippon et al., *J. Mol. Biol.* 75:369–375 (1973)

Robbins et al., *Cell* 64:615–623 (1991)

Rothstein, *Methods Enzymol.* 101:202–211 (1983)

Rott et al., *Virology* 165:74–86 (1988)

Russell et al., *EMBO J.* 2:1647–1653 (1983)

Sadler et al., *J. Cell Biol.* 109:2665–2675 (1989)

Sambrook et al., *Molecular Cloning: A Laboratory Manual*, 2nd Ed., Cold Spring Harbor Laboratory press, Cold Spring Harbor, N.Y., 1989

Sanger et al., *Proc. Natl. Acad. Sci. USA* 74:5463–5467 (1977)

Seeman et al., *Proc. Natl. Acad. Sci. USA* 73:804–808 (1976)

Seipke et al., *Biopolymers* 13:1621–1633 (1974)

Sharp et al., *Nucleic Acids Res.* 14:5125–5143 (1986)

Sherman et al., *Methods in Yeast Genetics*, Cold Spring Harbor Laboratory Press, Cold Spring Harbor, N.Y., 1986

St. Pierre et al., *Biopolymers* 17:1837–1847 (1978)

Studier et al., *Methods Enzymol.* 185:60–89 (1990)

Takeuchi et al., *FEBS Letters* 279:253–255 (1991)

Treco and Arnheim, *Mol. Cell Biol.* 6:3943–3947 (1986)

Trudelle, *Polymer* 16:9–15 (1975)

Tsao et al., *Cell* 56:111–118 (1989)

Vardimon and Rich, *Proc. Natl. Acad. Sci. USA* 81:3268–3272 (1983)

Wahls et al., *Mol. Cell Biol.* 10:785–793 (1990)

Winter and Varshavsky, *EMBO J.* 8:1867–1877 (1989)

Wittig et al., *J. Cell Biol.* 108:755–761 (1989)

Wood et al., *Proc. Natl. Acad. Sci. USA* 82:1585–1588 (1985)

Zinsmaier et al., *J. Neurogenet.* 7:15–29 (1990)

Zylicz et al., *EMBO J.* 8:1601–1608

Equivalents

Those skilled in the art will know, or be able to ascertain using no more than routine experimentation, many equivalents to the specific embodiments of the invention described herein. These and all other equivalents are intended to be encompassed by the following claims.

We claim:

1. A macroscopic membrane which is formed by self-assembly of amphiphilic peptides in an aqueous solution containing monovalent metal cations, wherein the peptides contain 12 or more amino acids, have alternating hydrophobic and hydrophilic amino acids and are complementary and structurally compatible.

2. The membrane of claim 1 wherein the peptides are homogeneous.

3. The membrane of claim 1 which is non-cytotoxic to mammalian cells.

4. The membrane of claim 1 wherein the hydrophilic amino acids are acidic and basic amino acids.

5. The membrane of claim 4 wherein the acidic amino acids are independently selected from the group consisting of aspartic acid and glutamic acid.

6. The membrane of claim 5 wherein the basic amino acids are independently selected from the group consisting of arginine, lysine, histidine and ornithine.

7. The membrane of claim 6 wherein the hydrophobic amino acids are selected from the group consisting of alanine, valine, leucine, isoleucine, methionine, phenylalanine, tyrosine, tryptophan, serine, threonine and glycine.

8. The membrane of claim 7 wherein the hydrophobic amino acids are alanine.

9. The membrane of claim 1 wherein the peptides are 12 to about 200 amino acids in length.

10. The membrane of claim 9 wherein the peptides are greater than 16 and less than about 200 amino acids.

11. The membrane of claim 1 wherein the peptides are soluble in aqueous solution in the absence of monovalent metal cations.

12. The membrane of claim 1 which is composed of β-sheets.

13. The membrane of claim 1 wherein the difference in interpeptide distance of the complementary peptides upon self-assembly is less than 3Å.

14. The membrane of claim 13 wherein the interpeptide distance is constant.

15. The membrane of claim 1 wherein the peptides are chemically synthesized.

16. The membrane of claim 1 wherein the monovalent metal cations are selected from the group consisting of $Li^+$, $Na^+$, $K^+$ and $Cs^+$.

17. The membrane of claim 16 wherein the monovalent metal cation is $Na^+$.

18. The membrane of claim 17 wherein the monovalent metal cation is added at a concentration of at least 5 mM.

19. The membrane of claim 1 wherein the peptides are present in the aqueous solution at a concentration of at least 1 mg/ml.

20. The membrane of claim 19 wherein the peptides are present in the aqueous solution at a concentration of at least about 10 mg/ml.

21. The membrane of claim 19 wherein the peptide is added to an aqueous solution containing monovalent metal cations.

22. The membrane of claim 1 wherein the membrane is stable in water at a temperature below the boiling point of the water.

23. The membrane of claim 22 wherein the CD spectra of the membrane is unaffected in water at a temperature below the boiling point of water.

24. The membrane of claim 1 wherein the membrane is unaffected at a pH from 1.5 to about 11.

25. The membrane of claim 24 wherein the pH profile of the membrane shows less than 10% decrease in ellipticity of the CD spectra by the treatment.

26. The membrane of claim 25 wherein the membrane is stable in aqueous solution containing less than about 10% sodium dodecyl sulfate, less than 7M guanidine hydrochloride, or less than 8M urea.

27. The membrane of claim 26 wherein the CD spectra is unaffected when the membrane is in aqueous solution containing less than about 10% sodium dodecyl sulfate, less than 7M guanidine hydrochloride, or less than 8M urea.

28. The membrane of claim 1 wherein the membrane is not degraded by trysin, α-chymotrypsin, papain, protease K or pronase.

29. The membrane of claim 1 wherein the membrane is stable in serum or ethanol.

30. The membrane of claim 1 wherein the peptides are selected from the group consisting of:
AKAKAEAEAKAKAEAE, (SEQ ID NO: 32);
AKAEAKAEAKAEAKAE, (SEQ ID NO: 33);
EAKAEAKAEAKAEAKA, (SEQ ID NO: 34);
KAEAKAEAKAEAKAEA, (SEQ ID NO: 35);
AEAKAEAKAEAKAEAK, (SEQ ID NO: 36);
ADADARARADADARAR, (SEQ ID NO: 37);
ARADARADARADARAD, (SEQ ID NO: 38);
DARADARADARADARA, (SEQ ID NO: 39);
RADARADARADARADA, (SEQ ID NO: 40);
ADARADARADARADAR, (SEQ ID NO: 41);
ARADAKAEARADAKAE, (SEQ ID NO: 42);
AKAEARADAKAEARAD, (SEQ ID NO: 43);
ARAKADAEARAKADAE, (SEQ ID NO: 44);
AKARAEADAKARADAE, (SEQ ID NO: 45);
AQAQAQAQAQAQAQAQ, (SEQ ID NO: 46);
VQVQVQVQVQVQVQVQ, (SEQ ID NO: 47);
YQYQYQYQYQYQYQYQ, (SEQ ID NO: 48);
HQHQHQHQHQHQHQHQ, (SEQ ID NO: 49);
ANANANANANANANAN, (SEQ ID NO: 50);
VNVNVNVNVNVNVNVN, (SEQ ID NO: 51);
YNYNYNYNYNYNYNYN, (SEQ ID NO: 52);
HNHNHNHNHNHNHNHN, (SEQ ID NO: 53),
ANAQANAQANAQANAQ, (SEQ ID NO: 54);
AQANAQANAQANAQAN, (SEQ ID NO: 55);
VNVQVNVQVNVQVNVQ, (SEQ ID NO: 56);
VQVNVQVNVQVNVQVN, (SEQ ID NO: 57);
YNYQYNYQYNYQYNYQ, (SEQ ID NO: 58);
YQYNYQYNYQYNYQYN, (SEQ ID NO: 59);
HNHQHNHQHNHQHNHQ, (SEQ ID NO: 60);
HQHNHQHNHQHNHQHN, (SEQ ID NO: 61);
AKAQADAKAQADAKAQAD, (SEQ ID NO: 19);
VKVQVDVKVQVDVKVQVD, (SEQ ID NO: 62);
YKYQYDYKYQYDYKYQYD, (SEQ ID NO: 63 ); and
HKHQHDHKHQHDHKHQHD, (SEQ ID NO: 64).

31. The membrane of claim 1 wherein the peptides are $(AEAEAKAK)_n$ (amino acids 310–317 of SEQ ID NO:2) and n is greater than or equal to 2.

32. The membrane of claim 1 wherein the peptides are $(ARARADAD)_n$ (amino acids 1–8 of SEQ ID No:3) and n is greater than or equal to 2.

33. The membrane of claim 1 wherein the peptides are $(RADARADA)_n$ (amino acids 1–8 of SEQ ID NO:40) and n is greater than or equal to 2.

34. A macroscopic membrane which is formed by self assembly of amphiphilic peptides in an aqueous solution containing monovalent metal cations; wherein the amphiphilic peptides are water-soluble, 12 to 200 amino acids in length, have alternating hydrophobic and hydrophilic amino acids, and are complementary and structurally compatible; and wherein the hydrophilic amino acids are complementary acidic and basic amino acids and the difference in interpeptide distance of the complementary peptides upon self-assembly is less than 3Å.

35. A macroscopic membrane formed by self-assembly of a peptide having the sequence (amino acid numbers 310 to 317 of SEQ ID NO:2) (Ala-Glu-Ala-Glu-Ala-Lys-Ala-Lys)$_n$, where n is greater than or equal to 2.

36. A macroscopic membrane formed by a peptide having the sequence (amino acid numbers 1 to 8 of SEQ ID NO:40) (Arg-Ala-Asp-Ala-Arg-Ala-Asp-Ala)$_n$, where n is greater than or equal to 2.

37. A method for forming a macroscopic membrane comprising forming an aqueous mixture of peptides, which are 12 or more amino acids in length, have alternating nonpolar and hydrophilic amino acids, and are complementary and structurally compatible, and monovalent metal cations under conditions suitable for self-assembly of the peptide into the macroscopic membrane and allowing the membrane to be formed.

38. The method of claim 37 wherein the peptides are homogeneous.

39. The method of claim 38 wherein the peptides have a sequence (amino acid numbers 310 to 317 of SEQ ID NO:2) (Ala-Glu-Ala-Glu-Ala-Lys-Ala-Lys)$_n$, where n is greater than or equal to 2.

40. The method of claim 38 wherein the peptides have a sequence amino acid numbers 1 to 8 of SEQ ID NO:3) (Ala-Arg-Ala-Arg-Ala-Asp-Ala-Asp)$_n$, where n is greater than or equal to 2.

41. The method of claim 38 wherein the peptide is chemically synthesized.

42. The method of claim 38 wherein the monovalent metal cations are selected from $Li^+$, $Na^+$, and $K^+$.

43. The method of claim 38 wherein the peptides are added to an aqueous solution containing the monovalent metal cations.

44. The method of claim 43 wherein the aqueous solution is phosphate-buffered saline.

45. The method of claim 38 wherein the suitable conditions comprise the absence of an inhibitor of the self-assembly of the peptides into the macroscopic membrane.

46. The method of claim 45 wherein the inhibitor is a divalent metal cation.

47. The method of claim 45 wherein the inhibitor is sodium dodecyl sulfate.

48. The method of claim 38 wherein the suitable conditions comprise a pH of less than 12.

* * * * *

UNITED STATES PATENT AND TRADEMARK OFFICE
CERTIFICATE OF CORRECTION

PATENT NO. : 5,670,483
DATED : September 23, 1997
INVENTOR(S) : Shuguang Zhang, Curtis Lockshin, Alexander Rich, and Todd Holmes It is certified that error appears in the above-identified patent and that said Letters Patent is hereby corrected as shown below:

In Column 65, line 16:  Delete "claim 38" and insert therefor --claim 37--;

In Column 66, line 1:   Delete "claim 38" and insert therefor --claim 37--;

In Column 66, line 3:   Delete "claim 38" and insert therefor --claim 37--;

In Column 66, line 8:   Delete "claim 38" and insert therefor --claim 37--; and

In Column 66, line 15:  Delete "claim 38" and insert therefor --claim 37--.

Signed and Sealed this

Seventeenth Day of March, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
( A ) LENGTH: 3083 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1292..2590
( D ) OTHER INFORMATION: /product="zuotin"

( x i ) SEQUENCE DESCRIPTION: SEQ ID NO:1:

```
CCAAAGTGAA TGATATGGGG CTAGAAACGT GTGTTACTTT AGGTATGGTT GATCAAGATC      60
AAGCAAAGCA ATTGAAAGAT GCAGGTTTGA CTGCATACAA CCATAACATC GACACTTCCA     120
GAGAACACTA TAGTAAGGTC ATCACCACGA GAACCTACGA CGACAGGTTA CAGACCATCA     180
AGAATGTCCA AGAATCTGGA ATAAAAGCCT GTACCGGTGG TATTTGGGT  CTCGGTGAAA     240
GCGAAGACGA CCATATAGGA TTCATCTACA CATTATCCAA TATGTCTCCT CATCCTGAGT     300
CCCTACCAAT TAATAGACTA GTTGCTATCA AAGGGACTCC AATGGCTGAG GAACTTGCCG     360
ATCCAAAGAG TAAAAAGTTG CAATTCGACG AAATTTTGAG AACCATTGCC ACAGCGAGAA     420
TAGTTATGCC AAAGGCCATT ATAAGACTTG CCGCTGGTCG TTATACAATG AAAGAAACAG     480
AGCAATTTGT CTGTTTCATG GCAGGTTGTA ACAGTATCTT CACCGGTAAG AAAATGCTGA     540
CGACAATATA TAACGGTTGG GACGAAGACA AGGCAATGTT GGCTAAATGG GGATTGCAAC     600
CTATGGAGGC ATTTAAGTAC GACAGATCTT GAAGATAGGG ATATGTGGAT AATTCTACGA     660
TTCTAACTGT ACATTTCTCC CTTATTTATT AAGAAAACCT ATATATATAT ATATTTACCT     720
ATTTATTCTG CCATCGTTAG CTGGCGTTTT ATCTTTTATG CATCCAATAT CTAATATTAC     780
TTCCGATCAC GCATTTAGTT CTGATTACAG CAGAAATCGT AGCGCGATGA GACATTTCAT     840
CAAATGGCCT TTTTTTTTTG GGCAATTTTT TTATATCTTG AAATGATAGT TGCCTTGTAC     900
TTTCAACCGT TCATTTCATT AAGAACTTGA CTAAATATGA ACATTTCTTA AAAAAAAAGG     960
TTGACATATA AAAATAATCG AATATAAACG ATGGAATTTT TATAAAATTA AACACATATA    1020
TATATATATA TTAACTATAA ATATGTCAAA GAAACCATAC AATCATAGAT TTATAACTAT    1080
CTTTTGGATG ACATTAATGA ACATAACGCT CCTAATACAA ATGTCAAAAA ATATTACCCG    1140
CAAATACGAA TCTTTTTTTT TTCTCGATGA AATTTTGCAA AGAGTTCGAA ATTTTTATTT    1200
CAAGAGCTGG TAGAGAAAAT TTCATAAGGT TTTCCTACCG ATGCTTTTAT AAAATCTTCG    1260
TTTTGTCTCA CATATACCAA CAAGAGTAAC G ATG TTT TCT TTA CCT ACC CTA       1312
                                 Met Phe Ser Leu Pro Thr Leu
                                  1               5

ACC TCA GAC ATC ACT GTT GAA GTC AAC AGT TCC GCT ACC AAA ACC CCA      1360
Thr Ser Asp Ile Thr Val Glu Val Asn Ser Ser Ala Thr Lys Thr Pro
      10                  15                  20

TTC GTC CGT CGT CCG GTC GAA CCG GTT GGT AAG TTC TTT TTG CAA CAT     1408
 Phe Val Arg Arg Pro Val Glu Pro Val Gly Lys Phe Phe Leu Gln His
      25                  30                  35

GCT CAA AGA ACT TTG AGA AAC CAC ACC TGG TCT GAA TTT GAA AGA ATT      1456
```

|  |  |  |  |  |  |  |  |  |  |  |  |  |  |  |  |
|---|---|---|---|---|---|---|---|---|---|---|---|---|---|---|---|
| Ala | Gln | Arg | Thr | Leu | Arg | Asn | His | Thr | Trp | Ser | Glu | Phe | Glu | Arg | Ile |
| 40 |  |  |  | 45 |  |  |  |  | 50 |  |  |  |  |  | 55 |

| GAA | GCT | GAA | AAG | AAC | GTC | AAA | ACC | GTT | GAT | GAA | TCC | AAT | GTC | GAC | CCA | 1504 |
|---|---|---|---|---|---|---|---|---|---|---|---|---|---|---|---|---|
| Glu | Ala | Glu | Lys | Asn | Val | Lys | Thr | Val | Asp | Glu | Ser | Asn | Val | Asp | Pro |  |
|  |  |  |  | 60 |  |  |  |  | 65 |  |  |  |  | 70 |  |  |

| GAT | GAG | TTG | TTA | TTC | GAC | ACT | GAA | TTG | GCC | GAT | GAA | GAT | TTA | CTG | ACT | 1552 |
|---|---|---|---|---|---|---|---|---|---|---|---|---|---|---|---|---|
| Asp | Glu | Leu | Leu | Phe | Asp | Thr | Glu | Leu | Ala | Asp | Glu | Asp | Leu | Leu | Thr |  |
|  |  |  | 75 |  |  |  |  | 80 |  |  |  |  | 85 |  |  |  |

| CAT | GAT | GCT | AGA | GAC | TGG | AAA | ACT | GCC | GAT | TTG | TAT | GCT | GCT | ATG | GGT | 1600 |
|---|---|---|---|---|---|---|---|---|---|---|---|---|---|---|---|---|
| His | Asp | Ala | Arg | Asp | Trp | Lys | Thr | Ala | Asp | Leu | Tyr | Ala | Ala | Met | Gly |  |
|  |  | 90 |  |  |  |  | 95 |  |  |  |  | 100 |  |  |  |  |

| TTG | TCT | AAG | TTG | CGT | TTC | AGA | GCT | ACT | GAA | AGT | CAA | ATC | ATC | AAG | GCT | 1648 |
|---|---|---|---|---|---|---|---|---|---|---|---|---|---|---|---|---|
| Leu | Ser | Lys | Leu | Arg | Phe | Arg | Ala | Thr | Glu | Ser | Gln | Ile | Ile | Lys | Ala |  |
|  | 105 |  |  |  |  | 110 |  |  |  |  | 115 |  |  |  |  |  |

| CAC | AGA | AAA | CAA | GTT | GTC | AAG | TAC | CAT | CCA | GAC | AAG | CAA | TCT | GCT | GCT | 1696 |
|---|---|---|---|---|---|---|---|---|---|---|---|---|---|---|---|---|
| His | Arg | Lys | Gln | Val | Val | Lys | Tyr | His | Pro | Asp | Lys | Gln | Ser | Ala | Ala |  |
| 120 |  |  |  |  | 125 |  |  |  |  | 130 |  |  |  |  | 135 |  |

| GGT | GGT | AGT | TTG | GAC | CAA | GAT | GGC | TTT | TTC | AAG | ATT | ATT | CAA | AAG | GCC | 1744 |
|---|---|---|---|---|---|---|---|---|---|---|---|---|---|---|---|---|
| Gly | Gly | Ser | Leu | Asp | Gln | Asp | Gly | Phe | Phe | Lys | Ile | Ile | Gln | Lys | Ala |  |
|  |  |  |  | 140 |  |  |  |  | 145 |  |  |  |  | 150 |  |  |

| TTT | GAA | ACT | TTG | ACT | GAT | TCC | AAC | AAG | AGA | GCT | CAG | TAC | GAC | TCA | TGT | 1792 |
|---|---|---|---|---|---|---|---|---|---|---|---|---|---|---|---|---|
| Phe | Glu | Thr | Leu | Thr | Asp | Ser | Asn | Lys | Arg | Ala | Gln | Tyr | Asp | Ser | Cys |  |
|  |  |  | 155 |  |  |  |  | 160 |  |  |  |  | 165 |  |  |  |

| GAT | TTT | GTT | GCC | GAT | GTT | CCT | CCT | CCA | AAG | AAG | GGT | ACC | GAT | TAT | GAC | 1840 |
|---|---|---|---|---|---|---|---|---|---|---|---|---|---|---|---|---|
| Asp | Phe | Val | Ala | Asp | Val | Pro | Pro | Pro | Lys | Lys | Gly | Thr | Asp | Tyr | Asp |  |
|  |  | 170 |  |  |  |  | 175 |  |  |  |  | 180 |  |  |  |  |

| TTT | TAT | GAA | GCT | TGG | GGC | CCC | GTT | TTC | GAA | GCT | GAA | GCT | CGT | TTT | TCT | 1888 |
|---|---|---|---|---|---|---|---|---|---|---|---|---|---|---|---|---|
| Phe | Tyr | Glu | Ala | Trp | Gly | Pro | Val | Phe | Glu | Ala | Glu | Ala | Arg | Phe | Ser |  |
|  | 185 |  |  |  |  | 190 |  |  |  |  | 195 |  |  |  |  |  |

| AAG | AAG | ACT | CCT | ATT | CCT | TCT | CTA | GGT | AAC | AAA | GAT | TCT | TCC | AAG | AAG | 1936 |
|---|---|---|---|---|---|---|---|---|---|---|---|---|---|---|---|---|
| Lys | Lys | Thr | Pro | Ile | Pro | Ser | Leu | Gly | Asn | Lys | Asp | Ser | Ser | Lys | Lys |  |
| 200 |  |  |  |  | 205 |  |  |  |  | 210 |  |  |  |  | 215 |  |

| GAA | GTT | GAA | CAA | TTC | TAT | GCT | TTC | TGG | CAC | AGA | TTT | GAC | TCC | TGG | AGA | 1984 |
|---|---|---|---|---|---|---|---|---|---|---|---|---|---|---|---|---|
| Glu | Val | Glu | Gln | Phe | Tyr | Ala | Phe | Trp | His | Arg | Phe | Asp | Ser | Trp | Arg |  |
|  |  |  |  | 220 |  |  |  |  | 225 |  |  |  |  | 230 |  |  |

| ACC | TTT | GAG | TTC | TTG | GAC | GAA | GAT | GTC | CCA | GAT | GAC | TCT | TCT | AAC | AGA | 2032 |
|---|---|---|---|---|---|---|---|---|---|---|---|---|---|---|---|---|
| Thr | Phe | Glu | Phe | Leu | Asp | Glu | Asp | Val | Pro | Asp | Asp | Ser | Ser | Asn | Arg |  |
|  |  |  | 235 |  |  |  |  | 240 |  |  |  |  | 245 |  |  |  |

| GAC | CAC | AAG | CGT | TAC | ATT | GAA | AGA | AAG | AAC | AAG | GCC | GCA | AGA | GAC | AAG | 2080 |
|---|---|---|---|---|---|---|---|---|---|---|---|---|---|---|---|---|
| Asp | His | Lys | Arg | Tyr | Ile | Glu | Arg | Lys | Asn | Lys | Ala | Ala | Arg | Asp | Lys |  |
|  |  | 250 |  |  |  |  | 255 |  |  |  |  | 260 |  |  |  |  |

| AAG | AAG | ACT | GCT | GAT | AAC | GCT | AGA | TTG | GTC | AAA | CTT | GTT | GAA | AGA | GCT | 2128 |
|---|---|---|---|---|---|---|---|---|---|---|---|---|---|---|---|---|
| Lys | Lys | Thr | Ala | Asp | Asn | Ala | Arg | Leu | Val | Lys | Leu | Val | Glu | Arg | Ala |  |
|  | 265 |  |  |  |  | 270 |  |  |  |  | 275 |  |  |  |  |  |

| GTC | AGT | GAA | GAT | CCC | CGT | ATC | AAA | ATG | TTC | AAA | GAA | GAA | GAG | AAG | AAG | 2176 |
|---|---|---|---|---|---|---|---|---|---|---|---|---|---|---|---|---|
| Val | Ser | Glu | Asp | Pro | Arg | Ile | Lys | Met | Phe | Lys | Glu | Glu | Glu | Lys | Lys |  |
| 280 |  |  |  |  | 285 |  |  |  |  | 290 |  |  |  |  | 295 |  |

| GAA | AAG | GAA | AGA | AGA | AAA | TGG | GAA | AGA | GAA | GCC | GGT | GCC | AGA | GCT | GAA | 2224 |
|---|---|---|---|---|---|---|---|---|---|---|---|---|---|---|---|---|
| Glu | Lys | Glu | Arg | Arg | Lys | Trp | Glu | Arg | Glu | Ala | Gly | Ala | Arg | Ala | Glu |  |
|  |  |  |  | 300 |  |  |  |  | 305 |  |  |  |  | 310 |  |  |

| GCT | GAA | GCT | AAG | GCC | AAG | GCC | GAA | GCT | GAA | GCG | AAG | GCT | AAA | GCT | GAA | 2272 |
|---|---|---|---|---|---|---|---|---|---|---|---|---|---|---|---|---|
| Ala | Glu | Ala | Lys | Ala | Lys | Ala | Glu | Ala | Glu | Ala | Lys | Ala | Lys | Ala | Glu |  |
|  |  |  | 315 |  |  |  |  | 320 |  |  |  |  | 325 |  |  |  |

| TCT | GAA | GCC | AAG | GCT | AAC | GCC | TCC | GCA | AAA | GCT | GAC | AAA | AAG | AAG | GCT | 2320 |
|---|---|---|---|---|---|---|---|---|---|---|---|---|---|---|---|---|
| Ser | Glu | Ala | Lys | Ala | Asn | Ala | Ser | Ala | Lys | Ala | Asp | Lys | Lys | Lys | Ala |  |
|  |  | 330 |  |  |  |  | 335 |  |  |  |  | 340 |  |  |  |  |

| AAG | GAA | GCT | GCT | AAG | GCC | GCC | AAG | AAA | AAG | AAC | AAG | AGA | GCC | ATC | CGT | 2368 |
|---|---|---|---|---|---|---|---|---|---|---|---|---|---|---|---|---|
| Lys | Glu | Ala | Ala | Lys | Ala | Ala | Lys | Lys | Lys | Asn | Lys | Arg | Ala | Ile | Arg |  |
| 345 |  |  |  |  | 350 |  |  |  |  | 355 |  |  |  |  |  |  |

| AAC | TCT | GCT | AAG | GAA | GCT | GAC | TAC | TTT | GGT | GAT | GCT | GAC | AAG | GCC | ACC | 2416 |
|---|---|---|---|---|---|---|---|---|---|---|---|---|---|---|---|---|

```
Asn  Ser  Ala  Lys  Glu  Ala  Asp  Tyr  Phe  Gly  Asp  Ala  Asp  Lys  Ala  Thr
360            365                      370                 375

ACG  ATT  GAC  GAA  CAA  GTT  GGT  TTG  ATC  GTT  GAC  AGT  TTG  AAT  GAC  GAA    2464
Thr  Ile  Asp  Glu  Gln  Val  Gly  Leu  Ile  Val  Asp  Ser  Leu  Asn  Asp  Glu
                    380                      385                      390

GAG  TTA  GTG  TCC  ACC  GCC  GAT  AAG  ATC  AAG  GCC  AAT  GCT  GCT  GGT  GCC    2512
Glu  Leu  Val  Ser  Thr  Ala  Asp  Lys  Ile  Lys  Ala  Asn  Ala  Ala  Gly  Ala
               395                      400                 405

AAG  GAA  GTT  TTG  AAG  GAA  TCT  GCA  AAG  ACT  ATT  GTC  GAT  TCT  GGC  AAA    2560
Lys  Glu  Val  Leu  Lys  Glu  Ser  Ala  Lys  Thr  Ile  Val  Asp  Ser  Gly  Lys
          410                      415                 420

CTA  CCA  TCC  AGC  TTG  TTG  TCC  TAC  TTC  GTG  TGAATACCGT AAGAAATGGA           2610
Leu  Pro  Ser  Ser  Leu  Leu  Ser  Tyr  Phe  Val
          425                 430

ATAGAATATA  TACGAATGTA  TACGAATATT  ATAGAGAACG  TTCTCTTTTA  TTTCTATAAT            2670

GAATAGGTTC  GGGTAACGGT  TCCCTTTTTA  GGTATTTCTA  GAAGATGAGA  GAAGAGGGAA            2730

TAATGAGAAA  GGCGAAAAAT  AAAGACACCT  TTAACGAAAG  ATCAAGGTG   TCCTTATTTA            2790

CTTACAATAG  CTGCAATTAG  TACGACTCAA  AAAAAGTGAA  AACAAAACTG  AAAGGATAGA            2850

TCAATGTCTT  ACAGAGGACC  TATTGGAAAT  TTTGGCGGAT  AGCCAATGTC  ATCATCGCTT            2910

GGACCATACT  CTGGCGGTGC  ACAATTCCGA  TCAAACCAGA  ACCAATCCAC  TTCTGGCATC            2970

TTAAAGCAAT  GGAAGCATTC  TTTTGAAAAG  TTTGCCTCCA  GAATTGAGGG  GCTCACTGAC            3030

AATGCAGTTG  TTTATAAATT  GAAGCCTTAC  ATTCCAAGTT  TGTCAAGATT  TTT                   3083
```

( 2 ) INFORMATION FOR SEQ ID NO:2:

( i ) SEQUENCE CHARACTERISTICS:
        ( A ) LENGTH: 433 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Phe  Ser  Leu  Pro  Thr  Leu  Thr  Ser  Asp  Ile  Thr  Val  Glu  Val  Asn
 1             5                     10                      15

Ser  Ser  Ala  Thr  Lys  Thr  Pro  Phe  Val  Arg  Arg  Pro  Val  Glu  Pro  Val
               20                     25                      30

Gly  Lys  Phe  Phe  Leu  Gln  His  Ala  Gln  Arg  Thr  Leu  Arg  Asn  His  Thr
          35                      40                      45

Trp  Ser  Glu  Phe  Glu  Arg  Ile  Glu  Ala  Glu  Lys  Asn  Val  Lys  Thr  Val
     50                      55                      60

Asp  Glu  Ser  Asn  Val  Asp  Pro  Asp  Glu  Leu  Leu  Phe  Asp  Thr  Glu  Leu
 65                 70                      75                      80

Ala  Asp  Glu  Asp  Leu  Leu  Thr  His  Asp  Ala  Arg  Asp  Trp  Lys  Thr  Ala
               85                      90                      95

Asp  Leu  Tyr  Ala  Ala  Met  Gly  Leu  Ser  Lys  Leu  Arg  Phe  Arg  Ala  Thr
               100                     105                     110

Glu  Ser  Gln  Ile  Ile  Lys  Ala  His  Arg  Lys  Gln  Val  Val  Lys  Tyr  His
          115                     120                     125

Pro  Asp  Lys  Gln  Ser  Ala  Ala  Gly  Gly  Ser  Leu  Asp  Gln  Asp  Gly  Phe
     130                     135                     140

Phe  Lys  Ile  Ile  Gln  Lys  Ala  Phe  Glu  Thr  Leu  Thr  Asp  Ser  Asn  Lys
145                      150                     155                     160

Arg  Ala  Gln  Tyr  Asp  Ser  Cys  Asp  Phe  Val  Ala  Asp  Val  Pro  Pro  Pro
               165                     170                     175
```

```
Lys Lys Gly Thr Asp Tyr Asp Phe Tyr Glu Ala Trp Gly Pro Val Phe
            180             185                 190
Glu Ala Glu Ala Arg Phe Ser Lys Lys Thr Pro Ile Pro Ser Leu Gly
        195             200             205
Asn Lys Asp Ser Ser Lys Lys Glu Val Glu Gln Phe Tyr Ala Phe Trp
    210             215             220
His Arg Phe Asp Ser Trp Arg Thr Phe Glu Phe Leu Asp Glu Asp Val
225             230             235                         240
Pro Asp Asp Ser Ser Asn Arg Asp His Lys Arg Tyr Ile Glu Arg Lys
                245             250             255
Asn Lys Ala Ala Arg Asp Lys Lys Thr Ala Asp Asn Ala Arg Leu
            260             265             270
Val Lys Leu Val Glu Arg Ala Val Ser Glu Asp Pro Arg Ile Lys Met
        275             280             285
Phe Lys Glu Glu Glu Lys Lys Glu Lys Glu Arg Arg Lys Trp Glu Arg
    290             295             300
Glu Ala Gly Ala Arg Ala Glu Ala Glu Ala Lys Ala Lys Ala Glu Ala
305             310             315                         320
Glu Ala Lys Ala Lys Ala Glu Ser Glu Ala Lys Ala Asn Ala Ser Ala
            325             330             335
Lys Ala Asp Lys Lys Lys Ala Lys Glu Ala Ala Lys Ala Ala Lys Lys
            340             345             350
Lys Asn Lys Arg Ala Ile Arg Asn Ser Ala Lys Glu Ala Asp Tyr Phe
        355             360             365
Gly Asp Ala Asp Lys Ala Thr Thr Ile Asp Glu Gln Val Gly Leu Ile
    370             375             380
Val Asp Ser Leu Asn Asp Glu Glu Leu Val Ser Thr Ala Asp Lys Ile
385             390             395                         400
Lys Ala Asn Ala Ala Gly Ala Lys Glu Val Leu Lys Glu Ser Ala Lys
            405             410             415
Thr Ile Val Asp Ser Gly Lys Leu Pro Ser Ser Leu Leu Ser Tyr Phe
            420             425             430
Val
```

( 2 ) INFORMATION FOR SEQ ID NO:3:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

```
Ala Arg Ala Arg Ala Asp Ala Asp Ala Arg Ala Arg Ala Asp Ala Asp
1               5               10                          15
```

( 2 ) INFORMATION FOR SEQ ID NO:4:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

```
Asp Ala Glu Phe Arg His Asp Ser Gly Tyr Glu Val His His Gln Lys
1               5               10                          15
```

```
      Leu  Val  Phe  Phe  Ala  Glu  Asp  Val  Gly  Ser  Asn  Lys
                     20                       25
```

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
      Gly  Ser  Asn  Lys  Gly  Ala  Ile  Ile  Gly  Leu  Met
      1                   5                        10
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
      Arg  Pro  Lys  Gln  Gln  Phe  Gly  Leu  Met
      1                   5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
      Arg  Pro  Lys  Pro  Gln  Gln  Trp  Leu  Leu
      1                   5
```

( 2 ) INFORMATION FOR SEQ ID NO:8:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
      Ala  Glu  Glu  Arg  Glu  Ile  Arg  Lys  Ala  Tyr  Lys  Arg  Leu  Ala  Met  Lys
      1                   5                        10                       15
      Tyr  His  Pro  Asp  Arg  Asn  Gln  Gly  Asp  Lys  Glu  Ala  Glu  Ala  Lys  Phe
                     20                       25                       30
      Lys  Glu  Ile  Lys  Glu  Ala  Tyr  Glu  Val  Leu  Thr  Asp  Ser  Gln  Lys  Arg
                     35                       40                       45
      Ala  Ala  Tyr  Asp
                     50
```

( 2 ) INFORMATION FOR SEQ ID NO:9:

( i ) SEQUENCE CHARACTERISTICS:
        ( A ) LENGTH: 52 amino acids
        ( B ) TYPE: amino acid
        ( D ) TOPOLOGY: linear (  i i  ) MOLECULE TYPE: protein (  x i  ) SEQUENCE DESCRIPTION: SEQ ID NO:9:

| Ala | Thr | Glu | Lys | Glu | Ile | Lys | Ser | Ala | Tyr | Arg | Gln | Leu | Ser | Lys | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | His | Pro | Asp | Lys | Asn | Ala | Gly | Ser | Glu | Glu | Ala | His | Gln | Lys | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | Glu | Val | Gly | Glu | Ala | Tyr | Asp | Val | Leu | Ser | Asp | Pro | Glu | Lys | Lys |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

Lys Ile Tyr Asp
        50

( 2 ) INFORMATION FOR SEQ ID NO:10:

( i ) SEQUENCE CHARACTERISTICS:
    ( A ) LENGTH: 52 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

| Ala | Thr | Gly | Asp | Asp | Ile | Lys | Lys | Thr | Tyr | Arg | Lys | Leu | Ala | Leu | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | His | Pro | Asp | Lys | Asn | Pro | Asp | Asn | Val | Asp | Ala | Ala | Asp | Lys | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Lys | Glu | Val | Asn | Arg | Ala | His | Ser | Ile | Leu | Ser | Asp | Gln | Thr | Lys | Arg |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

Asn Ile Tyr Asp
        50

( 2 ) INFORMATION FOR SEQ ID NO:11:

( i ) SEQUENCE CHARACTERISTICS:
    ( A ) LENGTH: 49 amino acids
    ( B ) TYPE: amino acid
    ( D ) TOPOLOGY: linear ( i i ) MOLECULE TYPE: protein ( x i ) SEQUENCE DESCRIPTION: SEQ ID NO:11:

| Ala | Asn | Glu | Gln | Glu | Leu | Lys | Lys | Gly | Tyr | Arg | Lys | Ala | Ala | Leu | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | His | Pro | Asp | Lys | Pro | Thr | Gly | Asp | Thr | Glu | Lys | Phe | Lys | Glu | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Glu | Ala | Phe | Glu | Ile | Leu | Asn | Asp | Pro | Gln | Lys | Arg | Glu | Ile | Tyr |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

Asp ( 2 ) INFORMATION FOR SEQ ID NO:12:

( i ) SEQUENCE CHARACTERISTICS:
    ( A ) LENGTH: 51 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

| Ala | Thr | Asp | Val | Glu | Ile | Lys | Lys | Ala | Tyr | Arg | Lys | Cys | Ala | Leu | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | His | Pro | Asp | Lys | Asn | Pro | Ser | Glu | Glu | Ala | Ala | Glu | Lys | Phe | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

```
            Glu  Ala  Ser  Ala  Ala  Tyr  Glu  Ile  Leu  Ser  Asp  Pro  Glu  Lys  Arg  Asp
                      35                      40                      45

Ile  Tyr  Asp
                 50
```

( 2 ) INFORMATION FOR SEQ ID NO:13:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Ala  Thr  Ala  Ala  Asp  Ile  Lys  Thr  Ala  Tyr  Arg  Arg  Thr  Ala  Leu  Lys
1                   5                        10                       15

Tyr  His  Pro  Asp  Lys  Gly  Gly  Asp  Glu  Glu  Lys  Met  Lys  Glu  Leu  Asn
              20                       25                       30

Thr  Leu  Met  Glu  Glu  Phe  Arg  Glu  Thr  Glu  Gly  Leu  Arg  Ala  Asp  Glu
         35                       40                       45

Thr  Leu  Glu  Asp  Ser  Asp
         50
```

( 2 ) INFORMATION FOR SEQ ID NO:14:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Ala  Ser  Asp  Arg  Asp  Ile  Lys  Ser  Ala  Tyr  Arg  Lys  Leu  Ser  Val  Lys
1                   5                        10                       15

Phe  His  Pro  Asp  Lys  Leu  Ala  Lys  Gly  Leu  Thr  Pro  Asp  Glu  Lys  Val
              20                       25                       30

Gln  Ile  Thr  Lys  Ala  Tyr  Glu  Ser  Leu  Thr  Asp  Glu  Leu  Val  Arg  Gln
         35                       40                       45

Asn  Tyr  Leu
         50
```

( 2 ) INFORMATION FOR SEQ ID NO:15:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Ala  Leu  Gly  Arg  Gly  Asp  Gln  Ala  Gly  Leu  Pro  Pro  Gly  Leu  Arg
1                   5                        10                       15

Tyr  His  Pro  Asp  Leu  Asn  Leu  Glu  Pro  Gly  Ala  Glu  Glu  Leu  Phe  Leu
              20                       25                       30

Glu  Ile  Ala  Glu  Ala  Tyr  Asp  Val  Leu  Ser  Asp  Pro  Arg  Leu  Arg  Glu
         35                       40                       45

Ile  Phe  Asp
         50
```

( 2 ) INFORMATION FOR SEQ ID NO:16:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Lys Ala Ala Ala Lys Arg Lys Ala Ala Leu Ala Lys Lys Lys Ala Ala
 1               5                  10                  15
Ala Ala Lys Arg Lys Ala Ala Ala Lys Ala Lys Lys Ala Lys Lys Pro
            20                  25                  30
Lys Lys Lys Ala Ala Lys Lys Ala Lys Lys Pro Ala Lys Lys Ser Pro
            35                  40                  45
Lys Lys Ala Lys Lys Pro Ala Lys Lys Ser Pro Lys
        50                  55                  60
```

( 2 ) INFORMATION FOR SEQ ID NO:17:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Lys Glu Lys Ala Pro Arg Lys Arg Ala Thr Ala Ala Lys Pro Lys Lys
 1               5                  10                  15
Pro Ala Ala Lys Lys Pro Ala Ala Ala Lys Lys Pro Lys Lys Ala
            20                  25                  30
Ala Ala Val Lys Lys Ser Pro Lys Lys Ala Lys Lys Pro Ala Ala Ala
            35                  40                  45
Ala Thr Lys Lys Ala Ala Lys Ser Pro Lys Lys Ala Ala
        50                  55                  60
```

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
CAAGAGTAAC CATGGTTTCT TTACC                                    25
```

( 2 ) INFORMATION FOR SEQ ID NO:19:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Ala Lys Ala Gln Ala Asp Ala Lys Ala Gln Ala Asp Ala Lys Ala Gln
 1               5                  10                  15
Ala Asp
```

( 2 ) INFORMATION FOR SEQ ID NO:20:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:20:

Val Arg Val Arg Val Asp Val Asp Val Arg Val Arg Val Asp Val Asp
1               5                   10                  15

( 2 ) INFORMATION FOR SEQ ID NO:21:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:21:

Ala Asp Ala Asp Ala Lys Ala Lys Ala Asp Ala Asp Ala Lys Ala Lys
1               5                   10                  15

( 2 ) INFORMATION FOR SEQ ID NO:22:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

ATGTTTTCTT TGCCAACTTT GACTTCTGAT AT                                32

( 2 ) INFORMATION FOR SEQ ID NO:23:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:23:

Met Val Ser Leu Pro Thr Leu Thr Ser Asp Ile
1               5                   10

( 2 ) INFORMATION FOR SEQ ID NO:24:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:24:

Ala Glu Ala Lys Ala Glu Ala Glu Ala Lys Ala Lys
1               5                   10

( 2 ) INFORMATION FOR SEQ ID NO:25:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:25:

```
Lys Ala Lys Ala Lys Ala Lys Ala Lys Ala Lys Ala Lys Ala Lys Ala
1               5                   10                  15
```

( 2 ) INFORMATION FOR SEQ ID NO:26:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Glu Ala Glu Ala Glu Ala Glu Ala Glu Ala Glu Ala Glu Ala Glu Ala
1               5                   10                  15
```

( 2 ) INFORMATION FOR SEQ ID NO:27:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Ala Asp Ala Asp Ala Asp Ala Asp Ala Asp Ala Asp Ala Asp Ala Asp
1               5                   10                  15
```

( 2 ) INFORMATION FOR SEQ ID NO:28:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( i x ) FEATURE:
        ( A ) NAME/KEY: negatively charged amino acid
        ( B ) LOCATION: 3, 5, 28, 42, 48

( i x ) FEATURE:
        ( A ) NAME/KEY: non-conserved amino acid
        ( B ) LOCATION: 4, 11, 24, 25, 26, 27, 30, 32, 35, 38, 39, 49,
                50, 53

( i x ) FEATURE:
        ( A ) NAME/KEY: non-polar amino acid
        ( B ) LOCATION: 14, 37, 43, 54

( x i ) SEQUENCE DESCRIPTION: SEQ ID NO:28:

```
Ala Thr Xaa Xaa Xaa Ile Lys Lys Ala Tyr Xaa Arg Lys Xaa Ala Leu
1               5                   10                  15

Lys Tyr His Pro Asp Lys Asn Xaa Xaa Xaa Xaa Xaa Ala Xaa Glu Xaa
                20                  25                  30

Lys Phe Xaa Glu Xaa Xaa Xaa Ala Tyr Xaa Xaa Leu Ser Asp Pro Xaa
            35                  40                  45

Xaa Xaa Lys Arg Xaa Xaa Tyr Asp
        50                  55
```

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

Lys Ala Lys Ala Lys
1               5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

Lys Ala His Ala Lys
1               5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: any amino acid
        ( B ) LOCATION: 5

( x i ) SEQUENCE DESCRIPTION: SEQ ID NO:31:

Lys Ala Lys Ala Xaa
1               5

( 2 ) INFORMATION FOR SEQ ID NO:32:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Ala Lys Ala Lys Ala Glu Ala Glu Ala Lys Ala Lys Ala Glu Ala Glu
1               5                   10                  15

( 2 ) INFORMATION FOR SEQ ID NO:33:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Ala Lys Ala Glu Ala Lys Ala Glu Ala Lys Ala Glu Ala Lys Ala Glu
1               5                   10                  15

( 2 ) INFORMATION FOR SEQ ID NO:34:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Glu Ala Lys Ala Glu Ala Lys Ala Glu Ala Lys Ala Glu Ala Lys Ala
1               5                   10                  15

( 2 ) INFORMATION FOR SEQ ID NO:35:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:

Lys Ala Glu Ala Lys Ala Glu Ala Lys Ala Glu Ala Lys Ala Glu Ala
1               5                   10                  15

( 2 ) INFORMATION FOR SEQ ID NO:36:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:36:

Ala Glu Ala Lys Ala Glu Ala Lys Ala Glu Ala Lys Ala Glu Ala Lys
1               5                   10                  15

( 2 ) INFORMATION FOR SEQ ID NO:37:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:37:

Ala Asp Ala Asp Ala Arg Ala Arg Ala Asp Ala Asp Ala Arg Ala Arg
1               5                   10                  15

( 2 ) INFORMATION FOR SEQ ID NO:38:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:38:

Ala Arg Ala Asp Ala Arg Ala Asp Ala Arg Ala Asp Ala Arg Ala Asp
1               5                   10                  15

( 2 ) INFORMATION FOR SEQ ID NO:39:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:39:

Asp Ala Arg Ala Asp Ala Arg Ala Asp Ala Arg Ala Asp Ala Arg Ala
1               5                   10                  15

( 2 ) INFORMATION FOR SEQ ID NO:40:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

```
Arg Ala Asp Ala Arg Ala Asp Ala Arg Ala Asp Ala Arg Ala Asp Ala
1               5                   10                  15
```

( 2 ) INFORMATION FOR SEQ ID NO:41:

( i ) SEQUENCE CHARACTERISTICS:
        ( A ) LENGTH: 16 amino acids
        ( B ) TYPE: amino acid
        ( C ) TOPOLOGY: linear ( x i ) SEQUENCE DESCRIPTION: SEQ ID NO:41:

```
Ala Asp Ala Arg Ala Asp Ala Arg Ala Asp Ala Arg Ala Asp Ala Arg
1               5                   10                  15
```

( 2 ) INFORMATION FOR SEQ ID NO:42:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

```
Ala Arg Ala Asp Ala Lys Ala Glu Ala Arg Ala Asp Ala Lys Ala Glu
1               5                   10                  15
```

( 2 ) INFORMATION FOR SEQ ID NO:43:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

```
Ala Lys Ala Glu Ala Arg Ala Asp Ala Lys Ala Glu Ala Arg Ala Asp
1               5                   10                  15
```

( 2 ) INFORMATION FOR SEQ ID NO:44:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

```
Ala Arg Ala Lys Ala Asp Ala Glu Ala Arg Ala Lys Ala Asp Ala Glu
1               5                   10                  15
```

( 2 ) INFORMATION FOR SEQ ID NO:45:

( i ) SEQUENCE CHARACTERISTICS:
        ( A ) LENGTH: 16 amino acids
        ( B ) TYPE: amino acid (D) TOPOLOGY: linear (ii) MOLECULE TYPE: peptide (xi) SEQUENCE DESCRIPTION: SEQ ID NO:45:

```
Ala Lys Ala Arg Ala Glu Ala Asp Ala Lys Ala Arg Ala Asp Ala Glu
1               5                   10                  15
```

(2) INFORMATION FOR SEQ ID NO:46:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:46:

```
Ala Gln Ala Gln Ala Gln Ala Gln Ala Gln Ala Gln Ala Gln Ala Gln
1               5                   10                  15
```

(2) INFORMATION FOR SEQ ID NO:47:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:47:

```
Val Gln Val Gln Val Gln Val Gln Val Gln Val Gln Val Gln Val Gln
1               5                   10                  15
```

(2) INFORMATION FOR SEQ ID NO:48:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:48:

```
Tyr Gln Tyr Gln Tyr Gln Tyr Gln Tyr Gln Tyr Gln Tyr Gln Tyr Gln
1               5                   10                  15
```

(2) INFORMATION FOR SEQ ID NO:49:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:49:

```
His Gln His Gln His Gln His Gln His Gln His Gln His Gln His Gln
1               5                   10                  15
```

(2) INFORMATION FOR SEQ ID NO:50:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:50:

```
Ala  Asn  Ala  Asn  Ala  Asn  Ala  Asn  Ala  Asn  Ala  Asn  Ala  Asn  Ala  Asn
1                 5                          10                         15
```

( 2 ) INFORMATION FOR SEQ ID NO:51:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:

```
Val  Asn  Val  Asn  Val  Asn  Val  Asn  Val  Asn  Val  Asn  Val  Asn  Val  Asn
1                 5                          10                         15
```

( 2 ) INFORMATION FOR SEQ ID NO:52:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:52:

```
Tyr  Asn  Tyr  Asn  Tyr  Asn  Tyr  Asn  Tyr  Asn  Tyr  Asn  Tyr  Asn  Tyr  Asn
1                 5                          10                         15
```

( 2 ) INFORMATION FOR SEQ ID NO:53:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:53:

```
His  Asn  His  Asn  His  Asn  His  Asn  His  Asn  His  Asn  His  Asn  His  Asn
1                 5                          10                         15
```

( 2 ) INFORMATION FOR SEQ ID NO:54:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:54:

```
Ala  Asn  Ala  Gln  Ala  Asn  Ala  Gln  Ala  Asn  Ala  Gln  Ala  Asn  Ala  Gln
1                 5                          10                         15
```

( 2 ) INFORMATION FOR SEQ ID NO:55:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:55:

```
Ala  Gln  Ala  Asn  Ala  Gln  Ala  Asn  Ala  Gln  Ala  Asn  Ala  Gln  Ala  Asn
1                 5                          10                         15
```

( 2 ) INFORMATION FOR SEQ ID NO:56:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

```
Val  Asn  Val  Gln  Val  Asn  Val  Gln  Val  Asn  Val  Gln  Val  Asn  Val  Gln
1                   5                        10                       15
```

( 2 ) INFORMATION FOR SEQ ID NO:57:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:57:

```
Val  Gln  Val  Asn  Val  Gln  Val  Asn  Val  Gln  Val  Asn  Val  Gln  Val  Asn
1                   5                        10                       15
```

( 2 ) INFORMATION FOR SEQ ID NO:58:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:58:

```
Tyr  Asn  Tyr  Gln  Tyr  Asn  Tyr  Gln  Tyr  Asn  Tyr  Gln  Tyr  Asn  Tyr  Gln
1                   5                        10                       15
```

( 2 ) INFORMATION FOR SEQ ID NO:59:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:59:

```
Tyr  Gln  Tyr  Asn  Tyr  Gln  Tyr  Asn  Tyr  Gln  Tyr  Asn  Tyr  Gln  Tyr  Asn
1                   5                        10                       15
```

( 2 ) INFORMATION FOR SEQ ID NO:60:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:60:

```
His  Asn  His  Gln  His  Asn  His  Gln  His  Asn  His  Gln  His  Asn  His  Gln
1                   5                        10                       15
```

( 2 ) INFORMATION FOR SEQ ID NO:61:

( i ) SEQUENCE CHARACTERISTICS:
        ( A ) LENGTH: 16 amino acids
        ( B ) TYPE: amino acid (D) TOPOLOGY: linear (ii) MOLECULE TYPE: peptide (xi) SEQUENCE DESCRIPTION: SEQ ID NO:61:

His Gln His Asn His Gln His Asn His Gln His Asn His Gln His Asn
    1               5                   10                  15

(2) INFORMATION FOR SEQ ID NO:62:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:62:

Val Lys Val Gln Val Asp Val Lys Val Gln Val Asp Val Lys Val Gln
    1               5                   10                  15

Val Asp (2) INFORMATION FOR SEQ ID NO:63:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:63:

Tyr Lys Tyr Gln Tyr Asp Tyr Lys Tyr Gln Tyr Asp Tyr Lys Tyr Gln
    1               5                   10                  15

Tyr Asp (2) INFORMATION FOR SEQ ID NO:64:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:64:

His Lys His Gln His Asp His Lys His Gln His Asp His Lys His Gln
    1               5                   10                  15

His Asp